(12) United States Patent
Kura

(10) Patent No.: US 8,758,228 B2
(45) Date of Patent: Jun. 24, 2014

(54) ENDOSCOPE SYSTEM, ENDOSCOPE SYSTEM CONTROL PROGRAM, AND ENDOSCOPE SYSTEM CONTROL METHOD

(75) Inventor: Yasuhito Kura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1583 days.

(21) Appl. No.: 11/914,497

(22) PCT Filed: May 12, 2006

(86) PCT No.: PCT/JP2006/309596
§ 371 (c)(1),
(2), (4) Date: Jan. 23, 2009

(87) PCT Pub. No.: WO2006/123590
PCT Pub. Date: Nov. 23, 2006

(65) Prior Publication Data
US 2009/0156896 A1 Jun. 18, 2009

(30) Foreign Application Priority Data
May 16, 2005 (JP) .................... PCT/JP2005/008912

(51) Int. Cl.
*A61B 1/04* (2006.01)

(52) U.S. Cl.
USPC ............ 600/115; 600/114; 600/118; 600/144

(58) Field of Classification Search
USPC .................................................. 600/115, 144
See application file for complete search history.

(56) References Cited

U.S. PATENT DOCUMENTS

| | | | |
|---|---|---|---|
| 4,040,413 A * | 8/1977 | Ohshiro .................... | 600/116 |
| 5,251,611 A * | 10/1993 | Zehel et al. ............... | 600/114 |
| 5,482,029 A * | 1/1996 | Sekiguchi et al. ......... | 600/109 |
| 6,203,494 B1 * | 3/2001 | Moriyama .................. | 600/144 |

(Continued)

FOREIGN PATENT DOCUMENTS

| | | |
|---|---|---|
| EP | 1 559 361 A2 | 8/2005 |
| JP | 05-091971 | 4/1993 |

(Continued)

OTHER PUBLICATIONS

Extended Supplementary Partial European Search Report dated Sep. 29, 2009.
Japanese Office Action dated Jun. 8, 2010.

*Primary Examiner* — Matthew J Kasztejna
(74) *Attorney, Agent, or Firm* — Scully, Scott, Murphy & Presser, P.C.

(57) ABSTRACT

An endoscope system includes an overtube (2) and an endoscope (1), where the overtube (2) is equipped with a shape-holding section (2b) capable of shape-holding and relaxing, a balloon (2a) provided at the distal end of the shape-holding section (2b) to fix the overtube (2) to a body cavity, and an endoscope passage hole (13) serving as a conduit through which the endoscope (1) is passed and the endoscope (1) is equipped with a shape-holding section (1b) capable of shape-holding and relaxing and a balloon (1a) provided at the distal end of the shape-holding section (1b) to fix the endoscope (1) to the body cavity. When one of the endoscope (1) and overtube (2) is inserted, the shape-holding section of the other shape-holds, and the body cavity is pulled with the balloon (1a) inflated, making it possible to reduce insertion length.

14 Claims, 17 Drawing Sheets

(56) References Cited

U.S. PATENT DOCUMENTS

| | | |
|---|---|---|
| 6,790,173 B2 * | 9/2004 | Saadat et al. ............... 600/114 |
| 7,695,428 B2 * | 4/2010 | Machida ..................... 600/114 |
| 7,955,253 B2 * | 6/2011 | Ewers et al. ................ 600/114 |
| 8,012,084 B2 * | 9/2011 | Machida ..................... 600/115 |
| 2002/0062062 A1 * | 5/2002 | Belson et al. ............... 600/146 |
| 2003/0233066 A1 * | 12/2003 | Ewers et al. ................. 604/27 |
| 2004/0186349 A1 | 9/2004 | Ewers et al. |
| 2005/0090709 A1 | 4/2005 | Okada et al. |
| 2005/0124855 A1 * | 6/2005 | Jaffe et al. .................. 600/114 |
| 2005/0124856 A1 * | 6/2005 | Fujikura et al. ............. 600/115 |
| 2005/0222496 A1 * | 10/2005 | Sekiguchi ................... 600/115 |

FOREIGN PATENT DOCUMENTS

| | | |
|---|---|---|
| JP | 11-290263 | 10/1999 |
| JP | 2002-369791 | 12/2002 |
| JP | 2004-33525 | 2/2004 |
| JP | 2004-209267 | 7/2004 |
| JP | 2004-337288 | 12/2004 |
| JP | 2004-358222 | 12/2004 |
| JP | 2005-46274 | 2/2005 |
| JP | 2005-46275 | 2/2005 |
| JP | 2005-46277 | 2/2005 |

* cited by examiner

ENDOSCOPE SYSTEM, ENDOSCOPE SYSTEM CONTROL PROGRAM, AND ENDOSCOPE SYSTEM CONTROL METHOD

TECHNICAL FIELD

The present invention relates to an endoscope system equipped with a plurality of elongate members movable relative to one another as well as an endoscope system control program and endoscope system control method.

BACKGROUND ART

When an endoscope is being inserted into a body cavity, organ pressure and the like produces a force tending to close the body cavity, which may make it difficult to insert the endoscope without aid. In such cases, a so-called endoscopic overtube (hereinafter referred to as an "overtube" where appropriate) is used widely. When inserted into the body cavity, for example, together with an endoscope, the overtube has the advantage of providing an insertion path into the body cavity for the endoscope, making it easy to insert and withdraw the endoscope subsequently.

In relation to endoscope systems made up of such an overtube and endoscope, there have been proposed various techniques for improving insertability of the endoscope into the deeper digestive tract such as the small and large intestines.

For example, Japanese Patent Laid-Open No. 2002-369791 describes a technique for providing a flexibility adjusting mechanism to an overtube to adjust hardness of the overtube, changing the hardness of the overtube according to hardness of the organs into which the overtube is inserted, and thereby improving insertability.

However, when inserting the endoscope into the deeper digestive tract using the overtube which is subject to hardness adjustment, since the endoscope is inserted along the intestines, an insertion section needs to be as long as the intestines. This means that when the endoscope is inserted into the large intestine, the insertion section needs to be approximately 2 m and that when the endoscope is inserted into the small intestine, the insertion section needs to be 5 m or longer. The long insertion section makes it troublesome to handle and difficult to operate the insertion section.

Japanese Patent Laid-Open No. 11-290263 describes an endoscope system made up of a combination of an endoscope and an overtube (sliding tube), in which a balloon is provided in a distal end portion of each of the endoscope and the overtube, and the endoscope is inserted through repeated inflation/deflation of each balloon and repeated insertion/withdrawal of the endoscope and overtube.

The technique described in Japanese Patent Laid-Open No. 11-290263 has the advantage of reducing the length of an insertion section compared to the length of the intestine because the technique shortens that part of the intestine which is lying on the hand side of the balloons by pulling the endoscope and overtube with the distal end portions of the endoscope and overtube fixed by the inflated balloons. However, since the technique inserts the endoscope and overtube into the deeper digestive tract using flexibility of the insertion section, both endoscope and overtube need to be flexible, and when pushing and inserting the endoscope or overtube, the endoscope and overtube can get bent, making it difficult to insert them.

The present invention has been made in view of the above circumstances and has an object to provide an endoscope system which is easy to insert, being equipped with a relatively short insertion section, as well as to provide an endoscope system control program and endoscope system control method for controlling the endoscope system.

DISCLOSURE OF INVENTION

Means for Solving the Problem

To achieve the above object, an endoscope system according to a first invention comprises a first elongate member inserted into a subject; a first shape-holding section provided on the first elongate member and capable of switching at least part of the first elongate member between a flexible and deformable first state and a shape-held second state; fixing means which, being provided at a distal end of the first elongate member, fixes the first elongate member to the subject by abutting the subject; a conduit which, being provided on the first elongate member, communicates a proximal opening and a distal opening of the first elongate member; a second elongate member which is inserted through the proximal opening, passed through the conduit in such a way that a distal end of the second elongate member can stick out of the distal opening, and movable relative to the first elongate member in a direction of the passage; and a second shape-holding section provided on at least part of the second elongate member in such a way as to include at least part of a portion which can stick out of the distal opening and capable of switching the at least part of the second elongate member between a flexible and deformable first state and a shape-held second state.

According to a second invention, in the endoscope system according to the first invention, the fixing means is provided beyond the first shape-holding section of the first elongate member.

According to a third invention, in the endoscope system according to the second invention, the fixing means is a balloon.

According to a fourth invention, in the endoscope system according to the second invention, the first elongate member is an insertion section of the endoscope.

According to a fifth invention, in the endoscope system according to the second invention, the second elongate member is an insertion section of the endoscope.

An endoscope system according to a sixth invention comprises a first elongate member inserted into a subject; a first shape-holding section provided on the first elongate member and capable of switching at least part of the first elongate member between a flexible and deformable first state and a shape-held second state; a conduit which, being provided on the first elongate member, communicates a proximal opening and a distal opening of the first elongate member; a second elongate member which is inserted through the proximal opening, passed through the conduit in such a way that a distal end of the second elongate member can stick out of the distal opening, and movable relative to the first elongate member in a direction of the passage; a second shape-holding section provided on at least part of the second elongate member in such a way as to include at least part of a portion which can stick out of the distal opening and capable of switching the at least part of the second elongate member between a flexible and deformable first state and a shape-held second state; and fixing means which, being provided at the distal end of the second elongate member, fixes the second elongate member to the subject by abutting the subject.

According to a seventh invention, in the endoscope system according to the sixth invention, the fixing means is provided beyond the second shape-holding section of the second elongate member.

According to an eighth invention, in the endoscope system according to the seventh invention, the fixing means is a balloon.

According to a ninth invention, in the endoscope system according to the seventh invention, the first elongate member is an insertion section of the endoscope.

According to a tenth invention, in the endoscope system according to the seventh invention, the second elongate member is an insertion section of the endoscope.

An endoscope system according to an eleventh invention comprises a first elongate member inserted into a subject; a first shape-holding section provided on the first elongate member and capable of switching at least part of the first elongate member between a flexible and deformable first state and a shape-held second state; first fixing means which, being provided at a distal end of the first elongate member, fixes the first elongate member to the subject by abutting the subject; a conduit which, being provided on the first elongate member, communicates a proximal opening and a distal opening of the first elongate member; a second elongate member which is inserted through the proximal opening, passed through the conduit in such a way that a distal end of the second elongate member can stick out of the distal opening, and movable relative to the first elongate member in a direction of the passage; a second shape-holding section provided on at least part of the second elongate member in such a way as to include at least part of a portion which can stick out of the distal opening and capable of switching the at least part of the second elongate member between a flexible and deformable first state and a shape-held second state; and second fixing means which, being provided at the distal end of the second elongate member, fixes the second elongate member to the subject by abutting the subject.

According to a twelfth invention, in the endoscope system according to the eleventh invention, the first fixing means is provided beyond the first shape-holding section of the first elongate member; and the second fixing means is provided beyond the second shape-holding section of the second elongate member.

According to a thirteenth invention, in the endoscope system according to the twelfth invention, the first fixing means and the second fixing means are both balloons.

According to a fourteenth invention, in the endoscope system according to the twelfth invention, the first elongate member is an insertion section of the endoscope.

According to a fifteenth invention, in the endoscope system according to the twelfth invention, the second elongate member is an insertion section of the endoscope.

According to a sixteenth invention, the endoscope system according to the twelfth invention farther comprises a control means which switches the second shape-holding section between the first state and the second state and fixes and unfixes the second elongate member to the subject by the second fixing means, wherein the control means switches the second shape-holding section from the second state to the first state with the second elongate member fixed to the subject by the second fixing means.

According to a seventeenth invention, the endoscope system according to the sixteenth invention further comprises guiding means which gives guidance as to a next operating step to be taken, wherein the control means further controls the guidance of the guiding means.

According to an eighteenth invention, in the endoscope system according to the seventeenth invention, the guiding means is display means which gives guidance by means of display.

According to a nineteenth invention, in the endoscope system according to the seventeenth invention, the guiding means is voice means which gives guidance by voice.

An endoscope system control program according to a twentieth invention is a program for making a computer control an endoscope system which comprises a first elongate member inserted into a subject, a first shape-holding section provided on the first elongate member and capable of switching at least part of the first elongate member between a flexible and deformable first state and a shape-held second state, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, a second shape-holding section provided on at least part of the second elongate member in such a way as to include at least part of a portion which can stick out of the distal opening and capable of switching the at least part of the second elongate member between a flexible and deformable first state and a shape-held second state, and second fixing means which, being provided at the distal end of the second elongate member, fixes the second elongate member to the subject by abutting the subject, the endoscope system control program comprising the steps of:

fixing the second elongate member to the subject by the second fixing means; and switching the second shape-holding section from the second state to the first state.

An endoscope system control method according to a twenty-first invention is a method for controlling an endoscope system which comprises a first elongate member inserted into a subject, a first shape-holding section provided on the first elongate member and capable of switching at least part of the first elongate member between a flexible and deformable first state and a shape-held second state, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, a second shape-holding section provided on at least part of the second elongate member in such a way as to include at least part of a portion which can stick out of the distal opening and capable of switching the at least part of the second elongate member between a flexible and deformable first state and a shape-held second state, and second fixing means which, being provided at the distal end of the second elongate member, fixes the second elongate member to the subject by abutting the subject, the endoscope system control method comprising the steps of:

fixing the second elongate member to the subject by the second fixing means; and switching the second shape-holding section from the second state to the first state.

BEST MODE FOR CARRYING OUT THE INVENTION

Embodiments of the present invention will be described below with reference to the drawings.

[First Embodiment]

Figure 1:
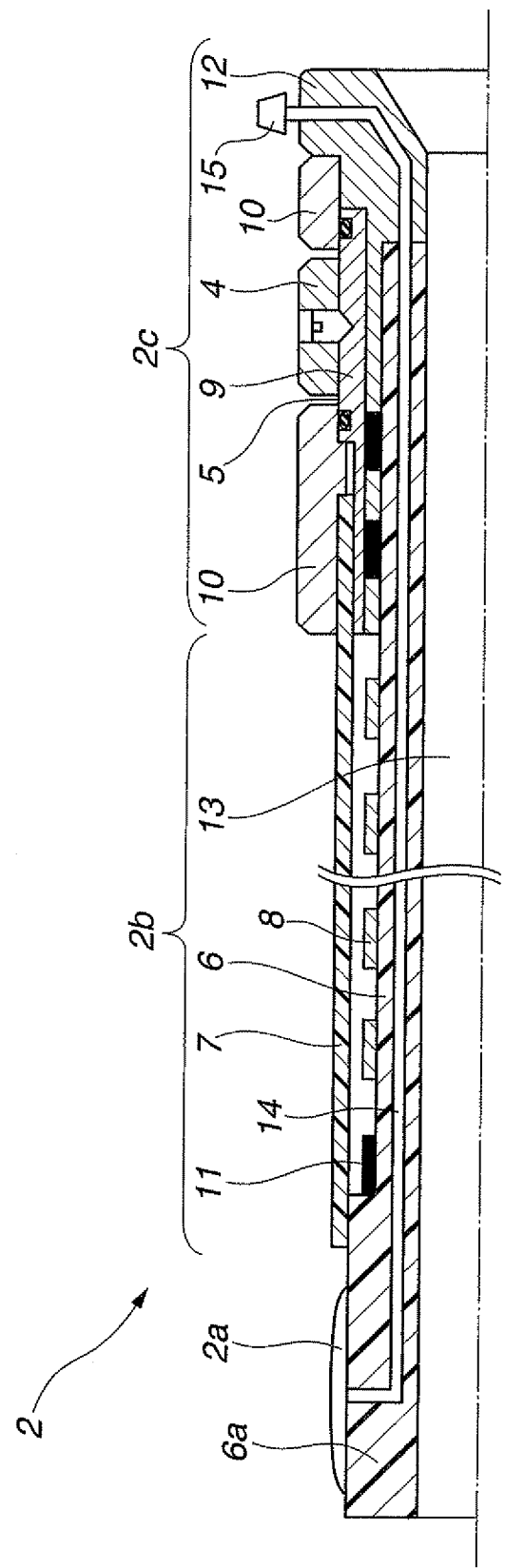
FIG. 1 is a sectional view taken along an insertion axis and showing a structure of an overtube according to a first embodiment of the present invention.
Figure 2:
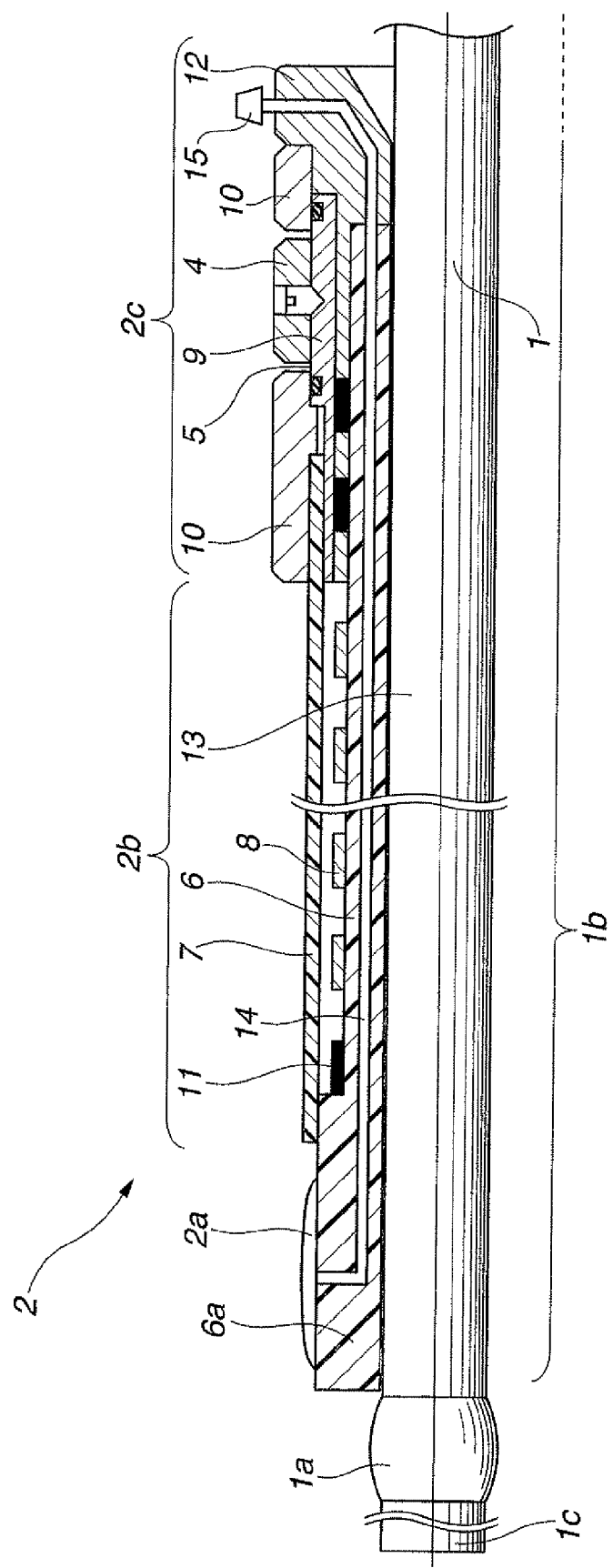
FIG. 2 is a sectional view showing the overtube according to the first embodiment with an endoscope inserted.
Figure 3:
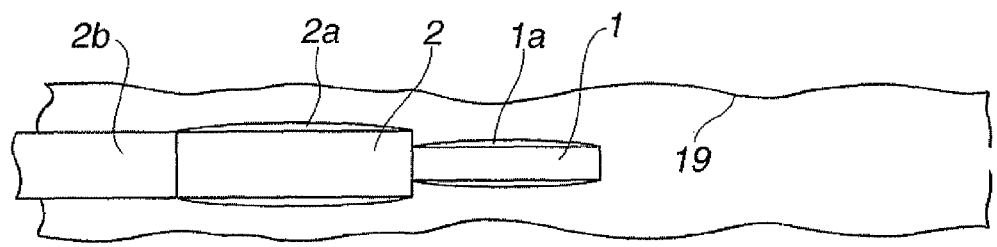
FIG. 3 is a diagram showing a first inserted state of an endoscope system according to the first embodiment.
Figure 4:
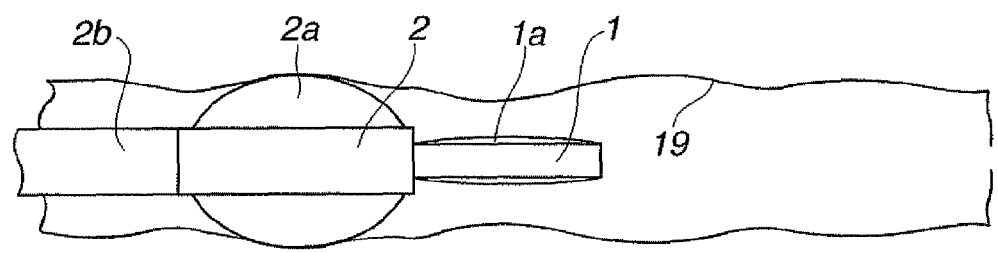
FIG. 4 is a diagram showing a second inserted state of the endoscope system according to the first embodiment.
Figure 5:
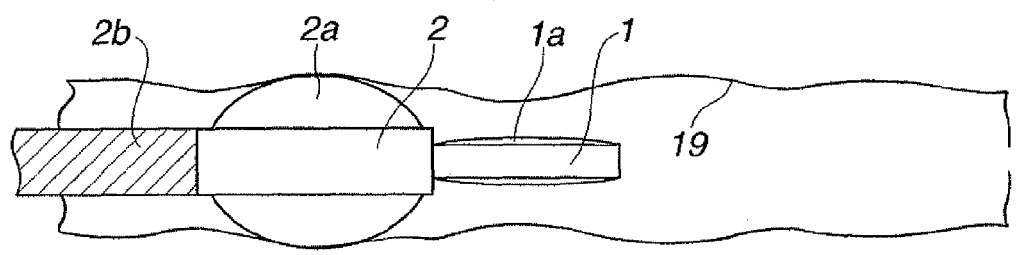
FIG. 5 is a diagram showing a third inserted state of the endoscope system according to the first embodiment.
Figure 6:
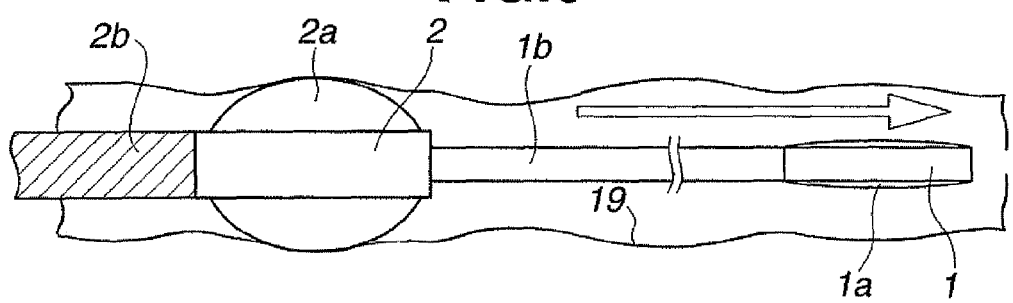
FIG. 6 is a diagram showing a fourth inserted state of the endoscope system according to the first embodiment.
Figure 7:
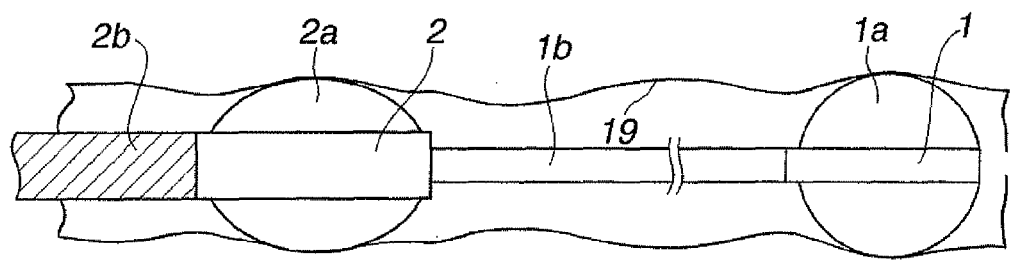
FIG. 7 is a diagram showing a fifth inserted state of the endoscope system according to the first embodiment.
Figure 8:
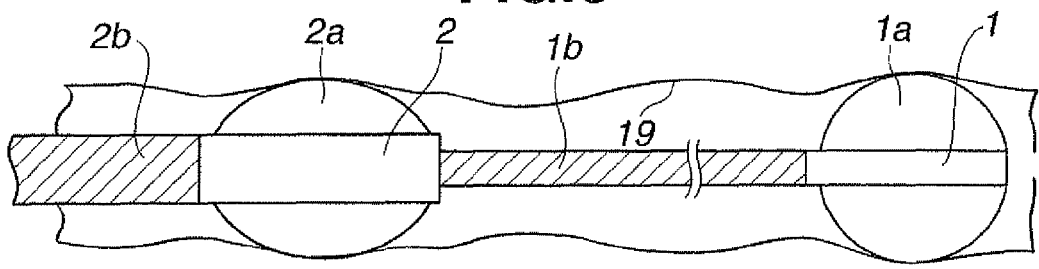
FIG. 8 is a diagram showing a sixth inserted state of the endoscope system according to the first embodiment.
Figure 9:
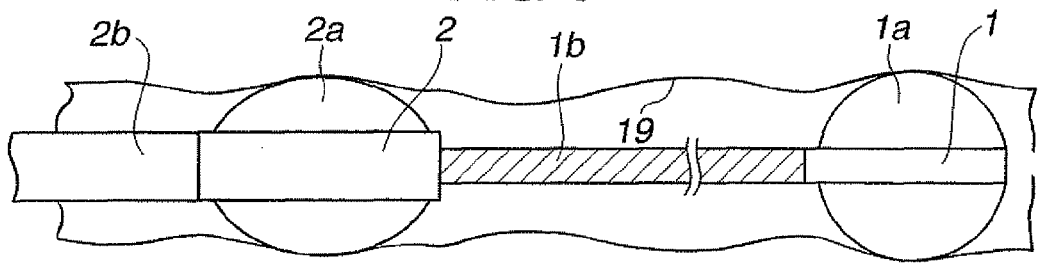
FIG. 9 is a diagram showing a seventh inserted state of the endoscope system according to the first embodiment.
Figure 10:
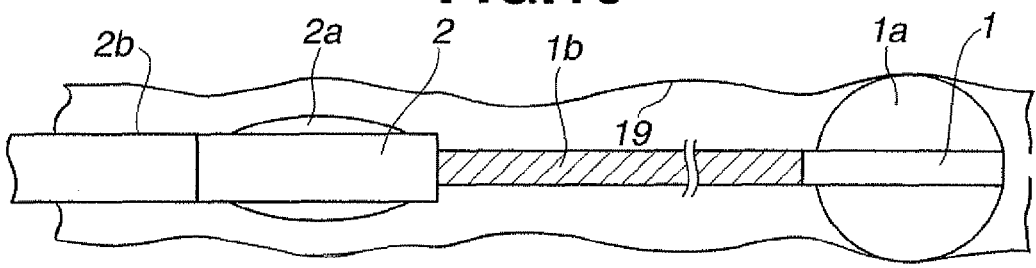
FIG. 10 is a diagram showing an eighth inserted state of the endoscope system according to the first embodiment.
Figure 11:
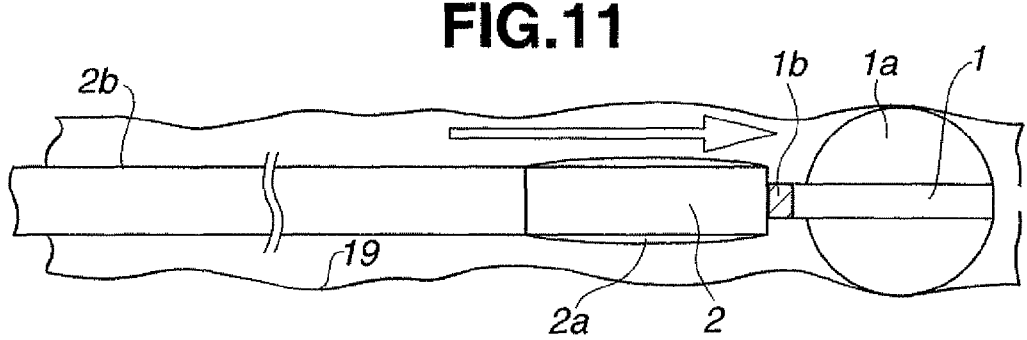
FIG. 11 is a diagram showing a ninth inserted state of the endoscope system according to the first embodiment.
Figure 12:
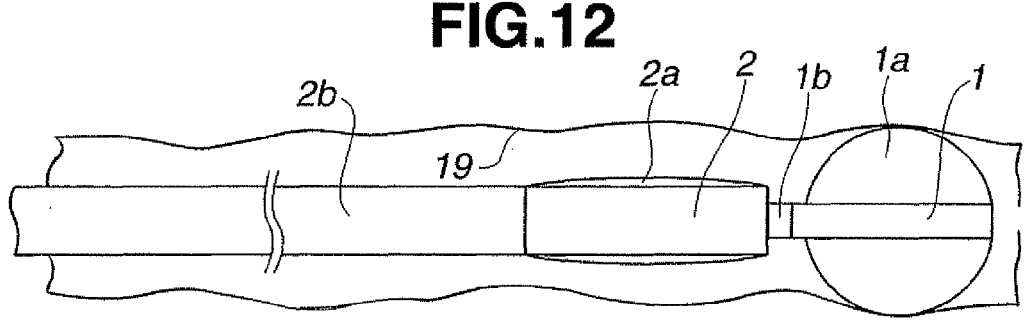
FIG. 12 is a diagram showing a tenth inserted state of the endoscope system according to the first embodiment.
Figure 13:
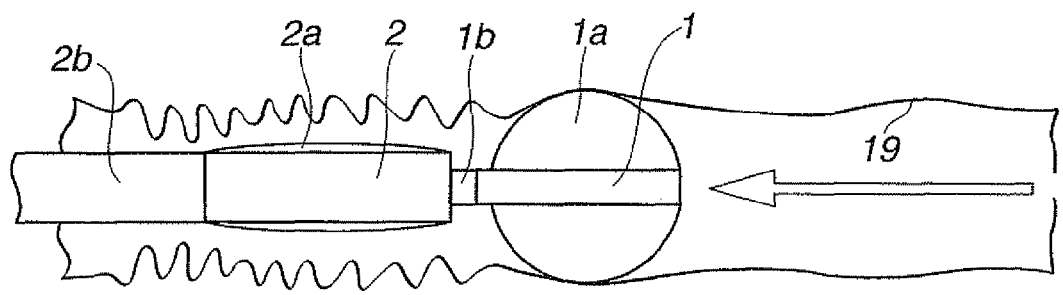
FIG. 13 is a diagram showing an eleventh inserted state of the endoscope system according to the first embodiment.
Figure 14:
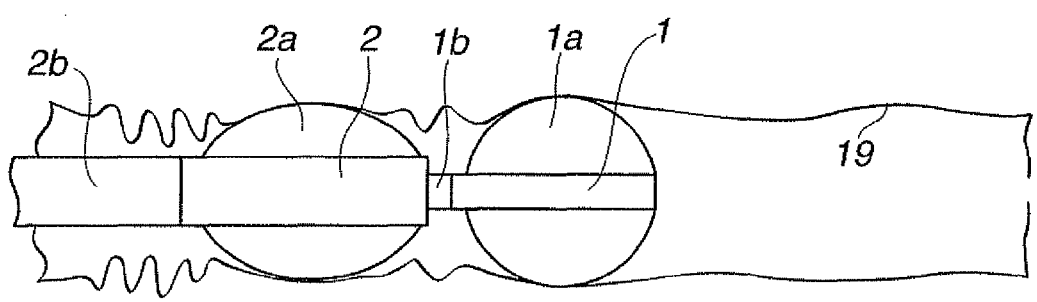
FIG. 14 is a diagram showing a twelfth inserted state of the endoscope system according to the first embodiment.
Figure 15:
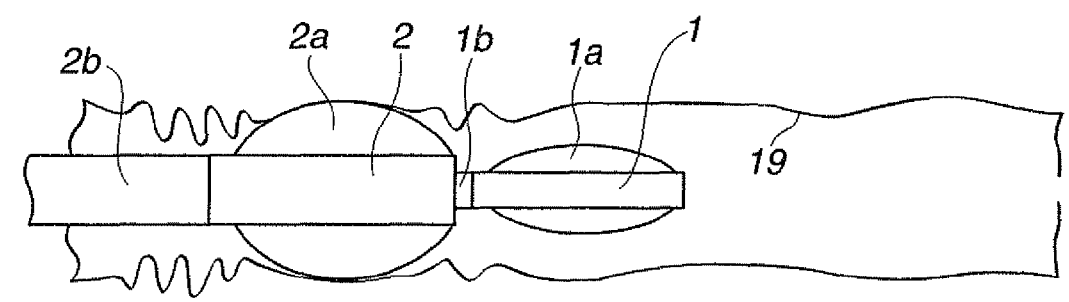
FIG. 15 is a diagram showing a thirteenth inserted state of the endoscope system according to the first embodiment.

FIGS. 1 to 15 show a first embodiment of the present invention, where FIG. 1 is a sectional view taken along an insertion axis and showing a structure of an overtube, FIG. 2 is a sectional view showing the overtube with an endoscope inserted, FIG. 3 is a diagram showing a first inserted state of an endoscope system, FIG. 4 is a diagram showing a second inserted state of the endoscope system, FIG. 5 is a diagram showing a third inserted state of the endoscope system, FIG. 6 is a diagram showing a fourth inserted state of the endoscope system, FIG. 7 is a diagram showing a fifth inserted state of the endoscope system, FIG. 8 is a diagram showing a sixth inserted state of the endoscope system, FIG. 9 is a diagram showing a seventh inserted state of the endoscope system, FIG. 10 is a diagram showing an eighth inserted state of the endoscope system, FIG. 11 is a diagram showing a ninth inserted state of the endoscope system, FIG. 12 is a diagram showing a tenth inserted state of the endoscope system, FIG. 13 is a diagram showing an eleventh inserted state of the endoscope system, FIG. 14 is a diagram showing a twelfth inserted state of the endoscope system, and FIG. 15 is a diagram showing a thirteenth inserted state of the endoscope system.

The endoscope system according to the present invention includes an endoscope 1 equipped with an insertion section which is an elongate member and an overtube 2 which is an elongate member through which the endoscope 1 is passed.

First, the overtube 2 will be described with reference to FIG. 1.

The overtube 2 configured as a tubular member includes an operation section 2c provided on the hand side and a shape-holding section 2b which, extending to the distal side, constitutes an insertion section.

The shape-holding section 2b includes a cylindrical inner sheath 6, a cylindrical outer sheath 7 with an inner surface larger in diameter than an outer surface of the inner sheath 6, and a friction member 8 placed between the inner sheath 6 and outer sheath 7.

The inner sheath 6 is made, for example, of a soft resin and the inside of the inner sheath 6 constitutes an endoscope passage hole 13 which serves as a conduit through which the endoscope 1 is passed.

The outer sheath 7 is similarly made, for example, of a soft resin and the inner surface of the outer sheath 7 constitutes a friction surface which produces a frictional force when brought into contact with the outer surface of the friction member 8.

The friction member 8 is made of a long, narrow plate member wound spirally into an approximately tubular shape. An outer surface of the friction member 8 constitutes a friction surface which produces a frictional force when brought into contact with the inner surface of the outer sheath 7. The friction member 8 is fixed to an inner periphery of the inner sheath 6 in a distal end portion along an insertion direction by a fixing section 11.

The operation section 2c includes a transmission member 9 which fixes the hand side of the friction member 8 and an operation lever 4 which is fixed to the transmission member 9, the transmission member 9 and operation lever 4 being supported in a carrier slot 5 in such a way as to be turnable in a circumferential direction (or both in circumferential and axial directions, as required), where the carrier slot 5 is provided between an inner sheath fixing member 12 which fixes the near end of the inner sheath 6 and an outer sheath fixing member 10 which fixes the near end of the outer sheath 7.

A balloon mount 6a is provided at the distal end of the shape-holding section 2b, for example, integrally with the inner sheath 6, and a balloon 2a which serves as fixing means is mounted on an outer periphery of the balloon mount 6a. In the inner sheath 6, an air line 14 communicated with the balloon 2a at one end is provided along a direction of the insertion axis. Running from the inner sheath 6 to the inner sheath fixing member 12, the air line 14 is communicated, at the other end, with an air supply port 15 provided on a side face of the inner sheath fixing member 12. Through the air line 14, air is supplied to the balloon 2a and gases are sucked out of the balloon 2a.

Unlike the shape-holding section 2b, the balloon mount 6a does not have a shape-holding function and is configured to be flexible. Consequently, the balloon 2a comes into close contact with body cavity walls when inflated.

The overtube 2 is configured to be shorter in total length than the insertion section of the endoscope 1.

Next, with reference to FIG. 2, description will be given of the endoscope 1 passed through the endoscope passage hole 13 of the overtube 2.

Being configured such that the insertion section which is an elongate member can be inserted through a proximal opening of the endoscope passage hole 13 that is conduit and passed through the endoscope passage hole 13 until a distal end can stick out of a distal opening of the endoscope passage hole 13, the endoscope 1 is capable of moving relative to the overtube 2 in a direction of passage.

The insertion section of the endoscope 1 has a shape-holding section 1b configured in a manner similar to the shape-holding section 2b of the overtube 2. A balloon 1a which is fixing means is mounted on an outer circumference beyond the shape-holding section 1b. Furthermore, a bending portion/distal end portion 1c is provided beyond the balloon 1a of the endoscope 1.

Again, the part of the endoscope 1 shown in FIG. 2 on which the balloon 1a is mounted does not have a shape-holding function and is configured to be flexible. Thus, again the balloon 1a comes into close contact with a body cavity wall when inflated.

Next, insertion procedures of the endoscope system will be described with reference to FIGS. 3 to 15. Incidentally, the bending portion/distal end portion 1c is not shown in FIGS. 3 to 15 for the sake of simplicity.

FIG. 3 shows a first inserted state at an initial stage of insertion. In this state, the shape-holding section 1b of the endoscope 1 and shape-holding section 2b of the overtube 2 are both relaxed to be in a flexible state, and the balloon 1a of the endoscope 1 and balloon 2a of the overtube 2 are both deflated. Only the distal-end side of the endoscope 1 with the balloon 1a extends outward from a tip of the overtube 2. This differs from a state described later in which the endoscope 1 is inserted and extends outward from the overtube 2.

Next, in the second inserted state shown in FIG. 4, the balloon 2a is inflated and brought into contact with a body cavity wall 19 by being supplied with air. At this stage, the surgeon may pull the overtube 2 and thereby check that the balloon 2a is fixed to the body cavity wall 19.

Next, in the third inserted state shown in FIG. 5, the shape-holding section 2b of the overtube 2 shape-holds. In FIGS. 5 to 10, parts which are shape-held are hatched.

Next, in the fourth inserted state shown in FIG. 6, the endoscope 1 is inserted into the overtube 2. Consequently, the endoscope 1 extends outward from the tip of the overtube 2. In so doing, since the overtube 2 is shape-held, the endoscope 1 can be inserted smoothly.

After the endoscope 1 is inserted by an appropriate length, in the fifth inserted state shown in FIG. 7, the balloon 1a is inflated and brought into close contact with the body cavity wall 19 by being supplied with air.

Furthermore, in the sixth inserted state shown in FIG. 8, the shape-holding section 1b of the endoscope 1 shape-holds.

Next, in the seventh inserted state shown in FIG. 9, the shape-holding section 2b of the overtube 2 relaxes.

Next, in the eighth inserted state shown in FIG. 10, the balloon 2a of the overtube 2 is deflated with air being sucked out of the balloon 2a.

Next, in the ninth inserted state shown in FIG. 11, the overtube 2 is inserted over the endoscope 1. Consequently, the tip of the overtube 2 approaches close to the hand side of the balloon 1a of the endoscope 1. In so doing, since the endoscope 1 is shape-held, the overtube 2 can be inserted smoothly.

Next, in the tenth inserted state shown in FIG. 12, the shape-holding section 1b of the endoscope 1 is relaxed. Consequently, now the shape-holding section 1b of the endoscope 1 and shape-holding section 2b of the overtube 2 have both been relaxed.

Next, in the eleventh inserted state shown in FIG. 13, as the surgeon pulls the endoscope 1 and overtube 2 integrally, the radius of curvature of the endoscope 1 and overtube 2 which are likely to have been bent along an insertion path increases, approaching a straight line. This removes excess flexing of the body cavity wall 19, for example, of the small intestine, reducing the length, along the insertion axis, of that part of the body cavity wall 19 which is lying on the hand side of the balloon 1a.

Furthermore, in the twelfth inserted state shown in FIG. 14, the balloon 2a of the overtube 2 is inflated and brought into close contact with the body cavity wall 19 by being supplied with air.

Next, in the thirteenth inserted state shown in FIG. 15, the balloon 1a of the endoscope 1 is deflated with air being sucked out of the balloon 1a.

Subsequently, through repetition of the third inserted state shown in FIG. 5 to the thirteenth inserted state shown in FIG. 15, the endoscope 1 and overtube 2 are advanced gradually in the body cavity wall 19.

When the endoscope 1 and overtube 2 are advanced to a desired position, it becomes possible to use the endoscope 1 for observation and treatment.

According to the first embodiment, the endoscope can be inserted easily because the overtube is shape-held during the insertion of the endoscope, and the overtube can be inserted easily because the endoscope is shape-held during the insertion of the overtube. Besides, since the body cavity wall is pulled in the eleventh inserted state shown in FIG. 13, it is possible to shorten the insertion portion, reducing complexity of insertion operation. This has the dual effect of shortening the insertion portion by means of a double-balloon system and making insertion easier due to shape-holding.

[Second Embodiment]

Figure 16:
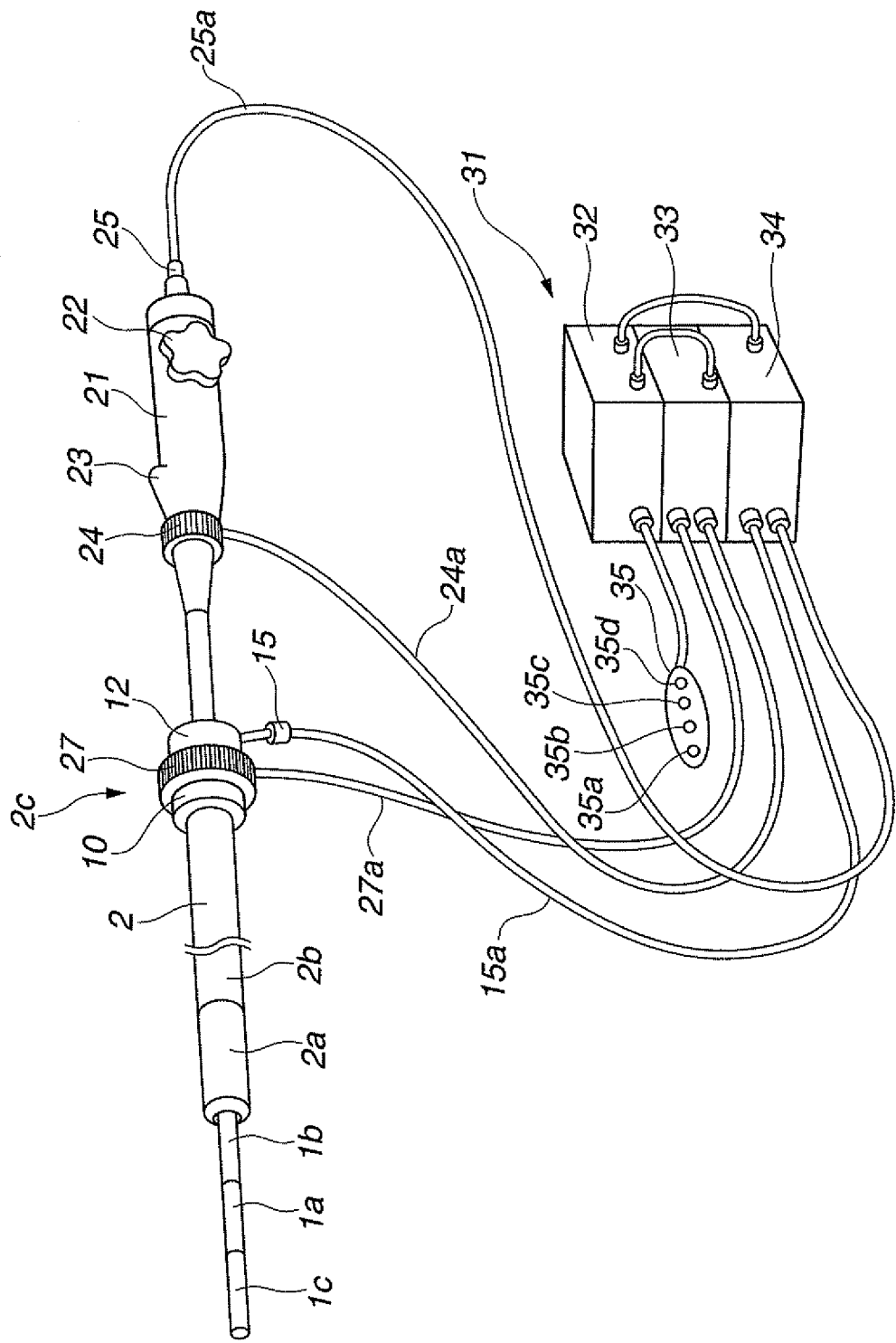
FIG. 16 is a diagram showing a configuration of an endoscope system according to a second embodiment of the present invention.
Figure 17:
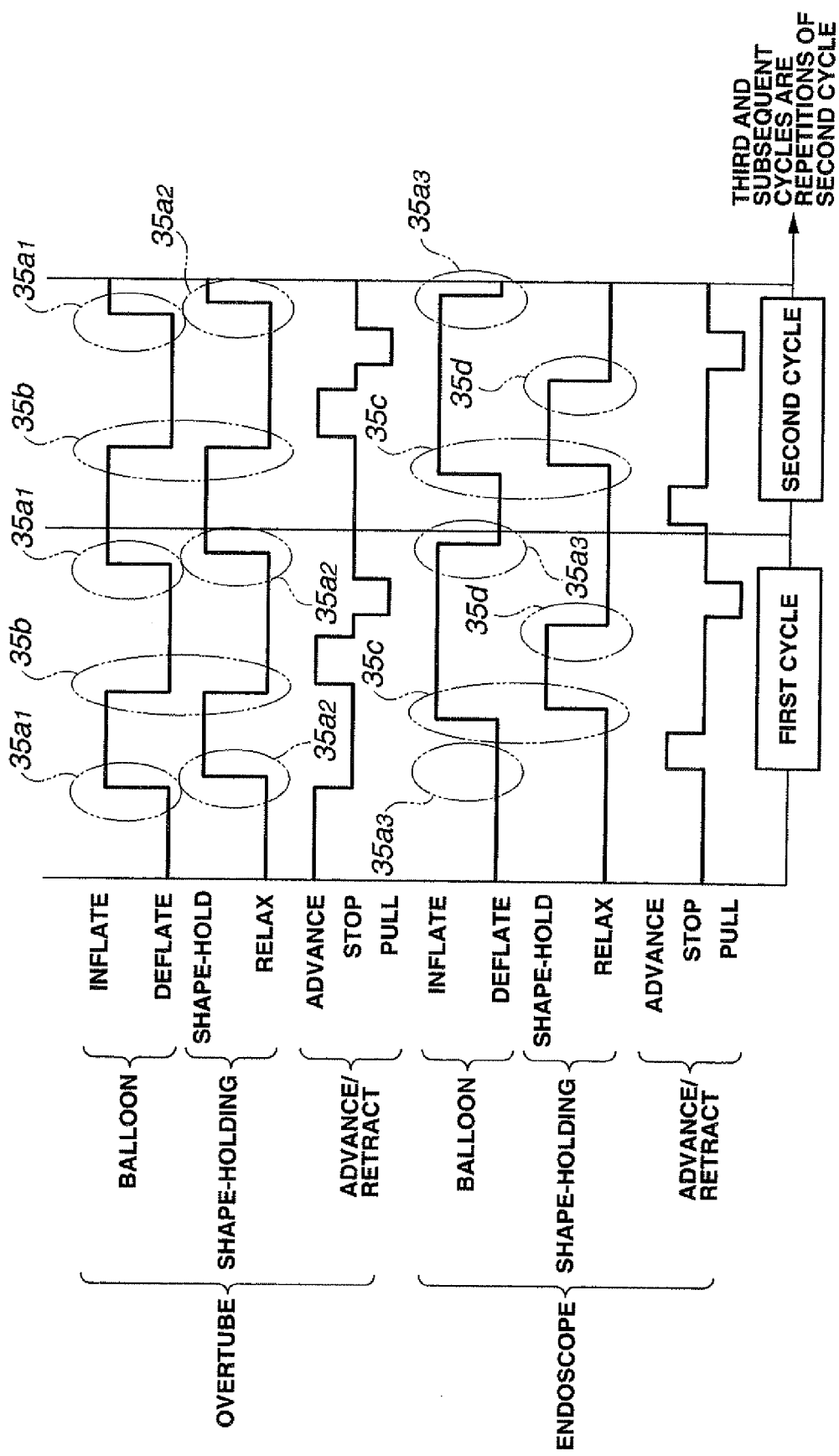
FIG. 17 is a chart showing action cycles of the endoscope system according to the second embodiment.
Figure 18:
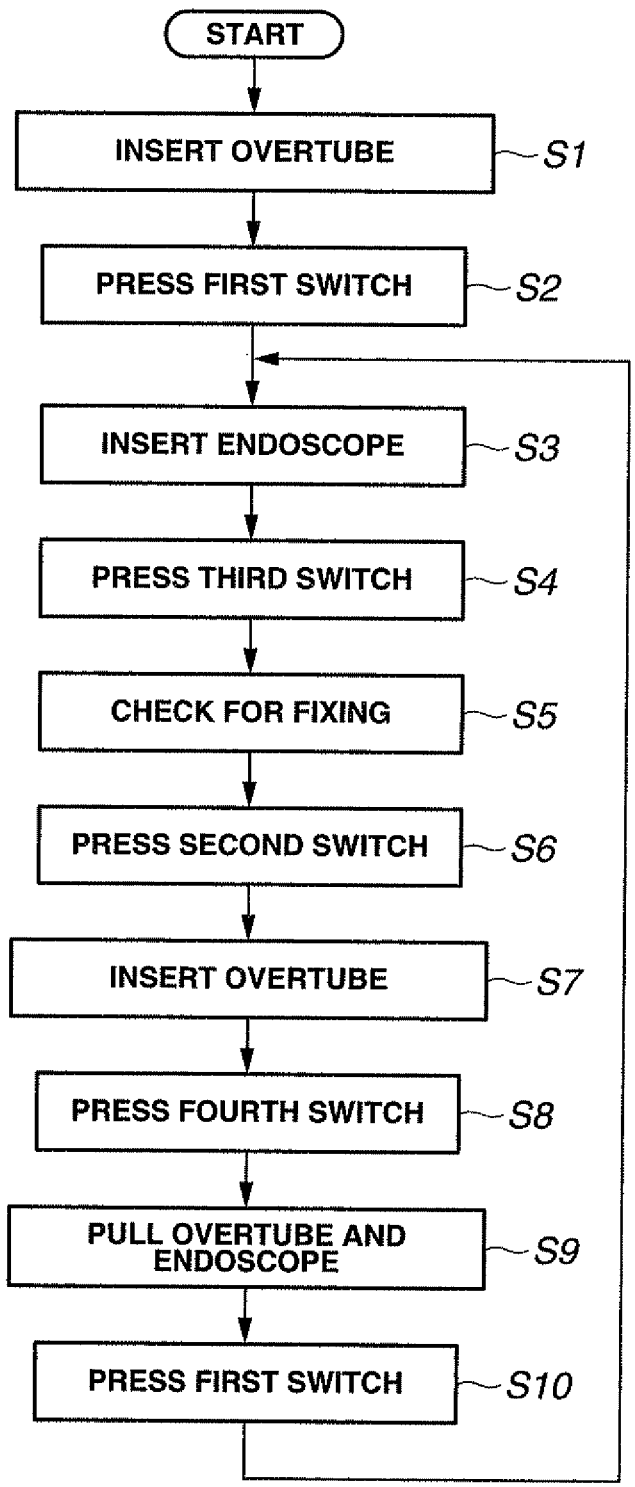
FIG. 18 is a flowchart showing processes of the endoscope system according to the second embodiment.
Figure 19:
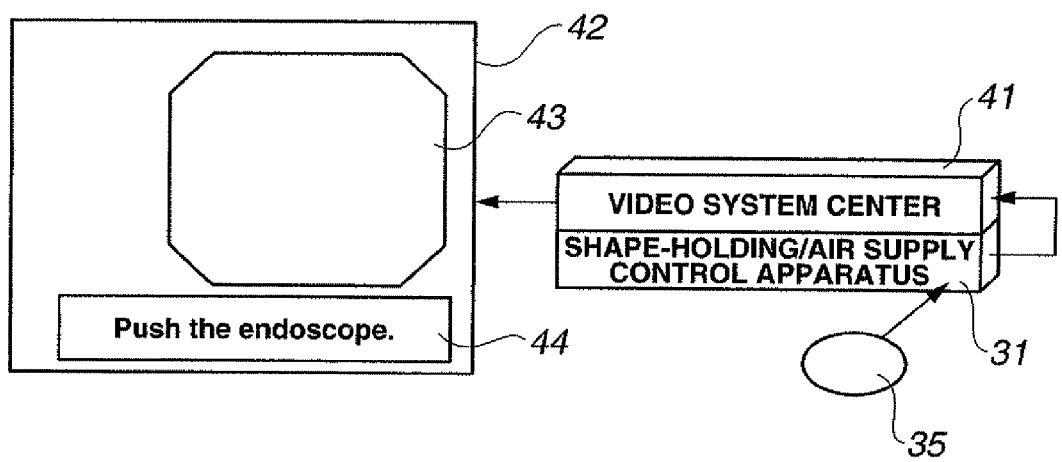
FIG. 19 is a diagram showing part of a variation to the endoscope system according to the second embodiment.
Figure 20:
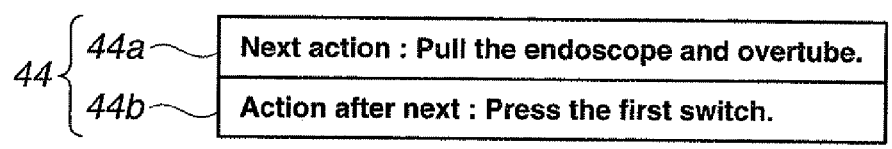
FIG. 20 is a diagram showing a display example of an operation method for the endoscope system on a monitor in the second embodiment.

FIGS. 16 to 20 show a second embodiment of the present invention, where FIG. 16 is a diagram showing a configuration of an endoscope system, FIG. 17 is a chart showing action cycles of the endoscope system, FIG. 18 is a flowchart showing processes of the endoscope system, FIG. 19 is a diagram showing part of a variation to the endoscope system, and FIG. 20 is a diagram showing a display example of an operation method for the endoscope system on a monitor.

In the second embodiment, the same components as those in the first embodiment will be denoted by the same reference numerals as the corresponding components in the first embodiment, and description thereof will be omitted and only differences from the first embodiment will be described mainly.

According to the second embodiment, the balloons 1a and 2a are inflated/deflated, and the endoscope 1 and the overtube 2 is shape-held/relaxed automatically.

First, configuration of the endoscope system will be described with reference to FIG. 16.

The endoscope 1 has an operation section on the hand side of the shape-holding section 1b of the insertion section. The operation section includes a grasping section 21 grasped by hand or the like, a bending operation section 22 used for bending operation of the bending portion/distal end portion 1c, a treatment instrument insertion port 23 used to insert a treatment instrument into a treatment instrument channel (not shown) in the insertion portion, and an air supply port 25 to which an air supply tube is connected to supply air to the balloon 1a.

Furthermore, the operation section of the endoscope 1 is equipped with a shape-holding/relaxing drive section 24 which automatically shape-holds and relaxes the shape-holding section 1b by turning a friction member in the shape-holding section 1b.

On the other hand, the operation section 2c of the overtube 2 is equipped with a shape-holding/relaxing drive section 27 which automatically shape-holds and relaxes the shape-holding section 2b by turning a friction member 8 in the shape-holding section 2b. The shape-holding/relaxing drive section 27 includes a driving source such as a motor whose driving force turns the operation lever 4. Incidentally, the shape-holding/relaxing drive section 24 of the endoscope 1 is configured substantially in a similar manner.

The endoscope 1 has a signal cable 24a connected to the shape-holding/relaxing drive section 24 and an air supply tube 25a connected to the air supply port 25. Also, the overtube 2 has a signal cable 27a connected to the shape-holding/relaxing drive section 27 and an air supply tube 15a connected to the air supply port 15.

Among them, the signal cables 24a and 27a are connected to a shape controller 33 of a shape-holding/air supply control apparatus 31 which is control means. On the other hand, the air supply tubes 15a and 25a are connected to an air supply controller 34 of the shape-holding/air supply control apparatus 31.

The shape controller 33 and air supply controller 34 are connected to and controlled by a main controller 32, which is connected to a switching section 35. The switching section 35 has four switches: a first switch 35a, second switch 35b, third switch 35c, and fourth switch 35d. Shape-holding/air supply control actions (described later) are performed according to operation of the switches.

Incidentally, although the shape-holding/air supply control apparatus 31 illustrated above includes the three components, namely, the main controller 32, shape controller 33, and air supply controller 34, these components may be constructed, of course, as an integral unit. Also, the number of switches in the switching section 35 is not limited to four.

Next, action of the endoscope system by means of the switching section 35 will be described with reference to FIGS. 17 and 18.

It is assumed that before the start of the action, the shape-holding section 1b of the endoscope 1 and shape-holding section 2b of the overtube 2 are both relaxed (made flexible) and the balloons 1a and 1b are both deflated.

When endoscopic procedures using the endoscope system are started, the surgeon inserts the overtube 2 by an appropriate length into the body cavity of the subject (Step S1).

The surgeon presses the first switch 35a (Step S2). Consequently, under the control of the main controller 32 which detects the press of the first switch 35a, the endoscope system performs a sequence of actions represented by the first iteration of symbols 35a1 to 35a3 in the first cycle in FIG. 17. That is, air is supplied from the air supply controller 34 to the balloon 2a of the overtube 2, inflating the balloon 2a as shown in FIG. 4 (symbol 35a1 in FIG. 17). Next, a drive signal is transmitted from the shape controller 33 to the shape-holding/relaxing drive section 27, causing the shape-holding section 2b to shape-hold as shown in FIG. 5 (symbol 35a2 in FIG. 17). Although the endoscope system is designed to perform the process of also deflating the balloon 1a of the endoscope 1 when the surgeon presses the first switch 35a, since the balloon 1a remains deflated immediately after the start of endoscopic procedures, practically nothing is done here.

When the state shown in FIG. 5 is reached, the surgeon inserts the endoscope 1 into the overtube 2 to achieve the state shown in FIG. 6 (Step S3).

Next, the surgeon presses the third switch 35c (Step S4). Consequently, under the control of the main controller 32 which detects the press of the third switch 35c, the endoscope system performs a sequence of actions represented by the first iteration of symbol 35c in the first cycle in FIG. 17. That is, air is supplied from the air supply controller 34 to the balloon 1a of the endoscope 1, inflating the balloon 1a as shown in FIG. 7. Next, a drive signal is transmitted from the shape controller 33 to the shape-holding/relaxing drive section 24, causing the shape-holding section 1b to shape-hold as shown in FIG. 8. Incidentally, the inflation of the balloon 1a and shape-holding of the shape-holding section 1b may be reversed in order.

When the state shown in FIG. 8 is reached, the surgeon may pull the endoscope 1 and thereby check whether the balloon 1a is fixed to the body cavity wall 19 (Step S5). However, Step S5 may be omitted. If Step S5 is omitted, the process in Step S4 described above, and a process in Step S6 described later can be carried out in succession automatically.

Subsequently, the surgeon presses the second switch 35b (Step S6). Consequently, under the control of the main controller 32 which detects the press of the second switch 35b, the endoscope system performs a sequence of actions represented by symbol 35b in the first cycle in FIG. 17. That is, a drive signal is transmitted from the shape controller 33 to the shape-holding/relaxing drive section 27, causing the shape-holding section 2b of the overtube 2 to relax as shown in FIG. 9. Also, the air supply controller 34 sucks air from the balloon 2a of the overtube 2, deflating the balloon 2a as shown in FIG. 10. Incidentally, the relaxation of the shape-holding section 2b and the deflation of the balloon 2a may be reversed in order.

When the state shown in FIG. 10 is reached, the surgeon inserts the overtube 2 over the endoscope 1 to achieve the state shown in FIG. 11 (Step S7).

Next, the surgeon presses the fourth switch 35d (Step S8). Consequently, under the control of the main controller 32 which detects the press of the fourth switch 35d, the endoscope system performs a sequence of actions represented by symbol 35d in the first cycle in FIG. 17. That is, a drive signal is transmitted from the shape controller 33 to the shape-holding/relaxing drive section 24, causing the shape-holding section 1b of the endoscope 1 to relax as shown in FIG. 12.

When the state shown in FIG. 12 is reached, the surgeon pulls the endoscope 1 and overtube 2 to shorten the body cavity wall 19 as shown in FIG. 13 (Step S9).

Next, when the surgeon presses the first switch 35a (Step S10), the endoscope system performs a sequence of actions represented by the second iteration of symbols 35a1 to 35a3 in the first cycle in FIG. 17. Consequently, the balloon 2a of the overtube 2 is inflated (FIG. 14), the balloon 1a of the endoscope 1 is deflated (FIG. 15), and the shape-holding section 2b of the overtube 2 shape-holds (FIG. 5).

Subsequently, a process in the second cycle is performed through repetition of the actions in Steps S3 to S10. Then, the same process as in the second cycle is repeated in the third and subsequent cycles.

Next, with reference to FIG. 19, description will be given of an exemplary configuration used to indicate a next operation to take to the surgeon. Incidentally, the endoscope 1 and overtube 2 are not shown in FIG. 19.

The shape-holding/air supply control apparatus 31 is connected to a video system center 41 and outputs information about the next operation to take to the video system center 41.

The video system center 41 is connected with a monitor 42 which is guiding means as well as display means. A screen of the monitor 42 displays a subject image 43 obtained by an image pickup device (not shown) of the endoscope 1 as well as displays the next operation to be taken by the surgeon as an operation guide display 44. In an example in FIG. 19, the surgeon is instructed to push the endoscope 1 next.

FIG. 20 shows an example in which the operation guide display 44 is provided for the next two steps.

That is, the operation guide display 44 includes a first operation guide display 44a which displays the next operation to take and a second operation guide display 44b which displays an operation to take after the next operation. In the example shown in FIG. 20, the next operation to take is to pull the endoscope 1 and overtube 2 and the operation after next is to press the first switch 35a.

Incidentally, although operation guidance is provided here for the next two steps, subsequent steps may be covered or an entire sequence of actions may be displayed with the current operation being highlighted or the like.

Although a monitor which is display means is used as the guiding means, the operation to take may be indicated by voice using voice means such as a speaker instead of, or in conjunction with, the monitor.

The shape-holding/air supply control apparatus 31 may be controlled by special-purpose hardware or controlled by general-purpose hardware with the application of an endoscope system control method. Alternatively, the apparatus may be equipped with computer functions and controlled by an endoscope system control program.

The second embodiment offers almost the same effect as the first embodiment. In addition, since shape-holding and air supply are controlled automatically, it is possible to insert the endoscope by means of an overtube by simply pressing, for example, four switches in sequence.

Since the next operation to take is indicated by display or by voice, the surgeon can perform the next operation with security and without mistakes.

Figure 38:
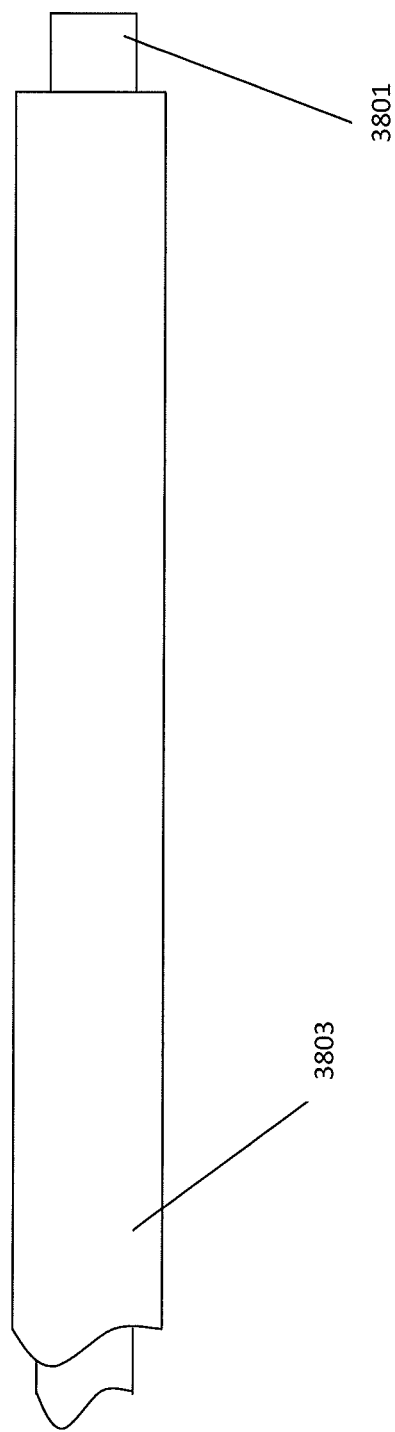
FIG. 38 is a diagram showing another embodiment of the present invention.

Although in the embodiments described above, the endoscope provided with a shape-holding function is inserted into the overtube provided with a shape-holding function, this is not restrictive and, with reference for example to FIG 38, an applicator 3801 which is an elongate member provided with a shape-holding function may be inserted, for example, into a channel of an endoscope 3803 provided with a shape-holding function. In that case, a balloon and the like similar to those described above will be provided in a distal end portion of the applicator.

Also, although in the embodiments described above, a balloon serving as fixing means is attached to each of the endoscope and overtube, the present invention is not limited to this. Even if a balloon is attached to only one of them, it is possible to reduce the insertion length by pulling the body cavity wall at least once.

Similarly, although both endoscope and overtube are provided with a shape-holding function in the above example, this is not restrictive. That is, even if only one of them is provided with a shape-holding function, it is possible to improve insertability.

In that case, since the inner elongate member (the endoscope in the above example) is generally inserted more deeply than the outer elongate member (the overtube in the above example), preferably that part of the inner elongate member which sticks out from the outer elongate member at the distal end is soft during insertion from the viewpoint of friendliness to the body cavity. Thus, if one of the inner and outer elongate members is provided with a shape-holding function, preferably that one is the inner elongate member.

On the other hand, if only the outer elongate member is provided with a shape-holding function, and if the outer elongate member is an overtube, a conventional endoscope not provided with a shape-holding function can be used as the inner elongate member, which is an advantage Furthermore, although balloons are used as fixing means in the above example, this is not restrictive. For example, a basket made up of multiple wires which can expand spherically or other means may be used as fixing means.

[Third Embodiment]

Figure 21:
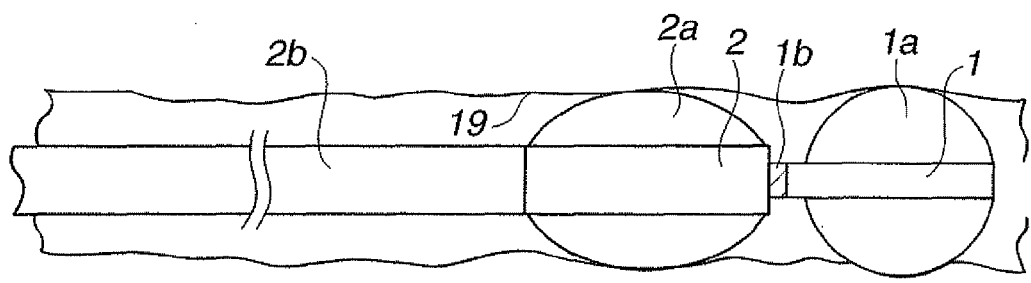
FIG. 21 is a diagram showing a tenth inserted state of an endoscope system according to a third embodiment of the present invention.
Figure 22:
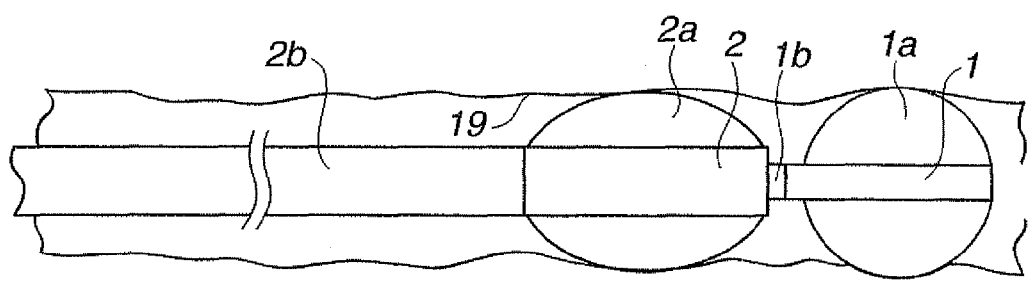
FIG. 22 is a diagram showing an eleventh inserted state of the endoscope system according to the third embodiment.
Figure 23:
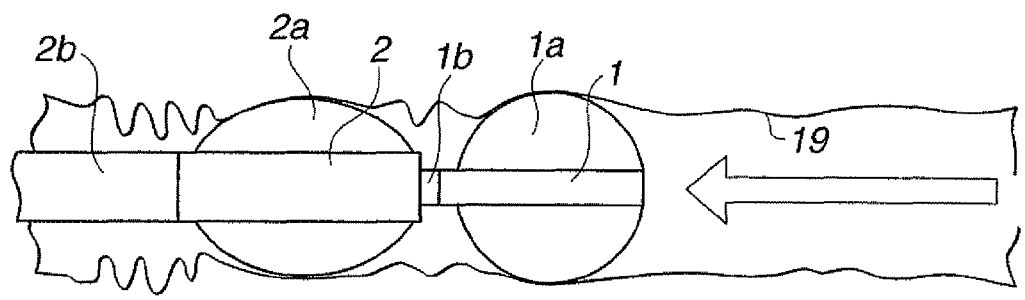
FIG. 23 is a diagram showing a twelfth inserted state of the endoscope system according to the third embodiment.

FIGS. 21 to 23 show a third embodiment of the present invention, where FIG. 21 is a diagram showing a tenth inserted state of an endoscope system, FIG. 22 is a diagram showing an eleventh inserted state of the endoscope system, and FIG. 23 is a diagram showing a twelfth inserted state of the endoscope system.

In the third embodiment, the same components as those in the first and second embodiments will be denoted by the same reference numerals as the corresponding components in the first and second embodiments, and description thereof will be omitted and only differences from the first and second embodiments will be described mainly.

The endoscope system according to the present embodiment has the same configuration as the first embodiment, but differs in the method for use and in operating procedures.

Once the surgeon starts insertion of the endoscope system, insertion procedures such as described with reference to FIG. 3 (first inserted state) to FIG. 11 (ninth inserted state) are carried out. It is assumed that the ninth inserted state shown in FIG. 11 has been reached.

In the tenth inserted state shown in FIG. 21, the balloon 2a is inflated and brought into close contact with the body cavity wall 19 by being supplied with air.

Next, in the eleventh inserted state shown in FIG. 22, the shape-holding section 1b of the endoscope 1 is relaxed. Consequently, now the shape-holding section 1b of the endoscope 1 and shape-holding section 2b of the overtube 2 have both been relaxed.

Next, in the twelfth inserted state shown in FIG. 23, the surgeon pulls the endoscope 1 and overtube 2 integrally, hauling in the body cavity wall 19, for example, of the small intestine and thereby reducing the length, along the insertion axis, of that part of the body cavity wall 19 which is lying on the hand side of the balloon 1a.

Next, in the thirteenth inserted state shown in FIG. 15, the balloon 1a of the endoscope 1 is deflated.

Subsequently, returning to the third inserted state in FIG. 5, the shape-holding section 2b of the overtube 2 shape-holds.

In this way, by repeating the procedures of FIG. 5→FIG. 6→FIG. 7→FIG. 8→FIG. 9→FIG. 10→FIG. 11→FIG. 21→FIG. 22→FIG. 23→FIG. 15→FIG. 5, it is possible to gradually advance the endoscope 1 and overtube 2 relative to the body cavity wall 19.

The third embodiment offers substantially the same effect as the first embodiment. In addition, when pulling the endoscope 1 and overtube 2 integrally, since the balloon 1a of the endoscope 1 and balloon 2a of the overtube 2 are in close contact with the body cavity wall 19, the surgeon can haul the body cavity wall 19 toward the hand side by holding the body cavity wall 19 more reliably.

[Fourth Embodiment]

Figure 24:
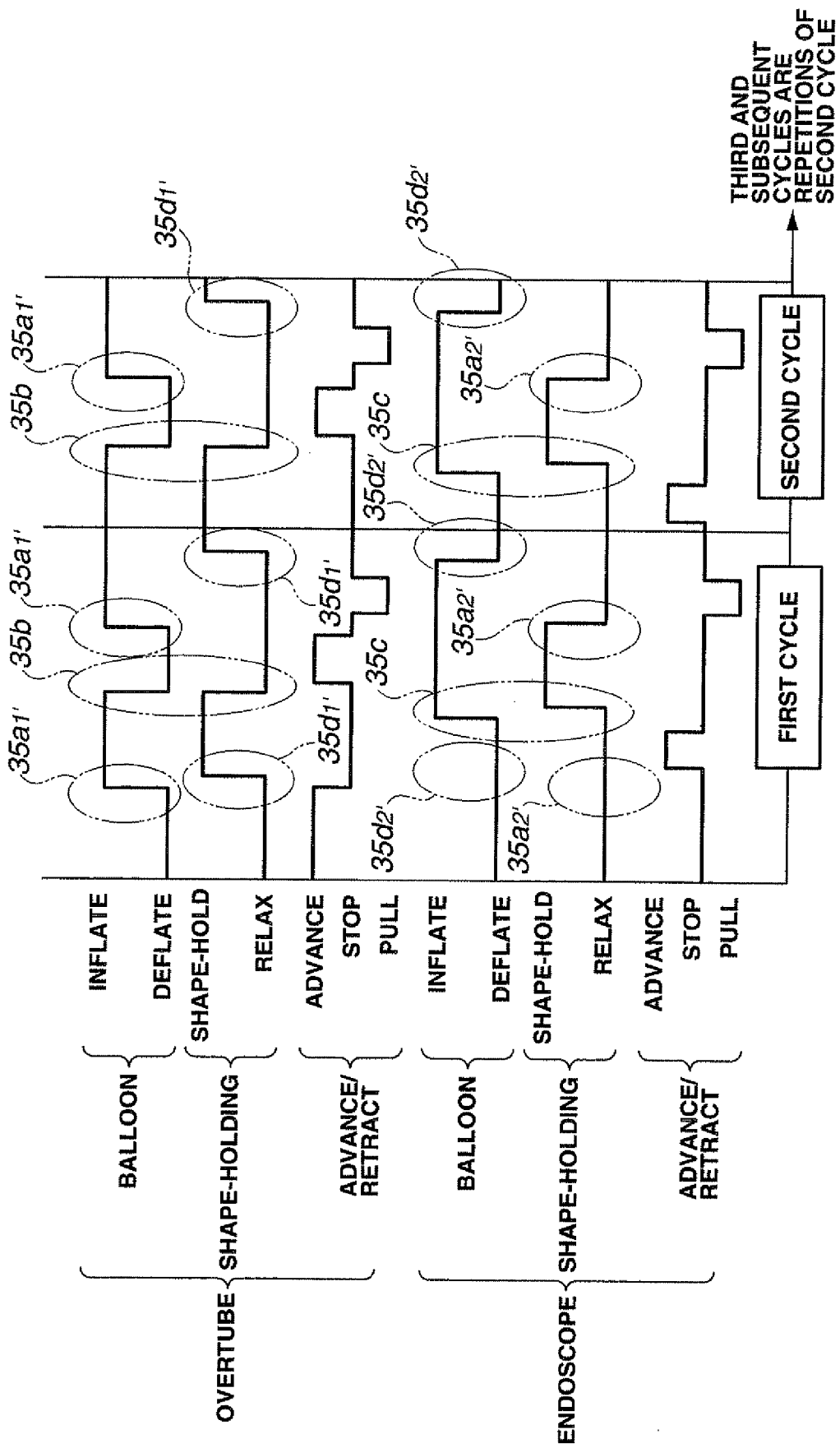
FIG. 24 is a chart showing action cycles of an endoscope system according to a fourth embodiment of the present invention.

FIG. 24, which shows a fourth embodiment of the present invention, is a chart showing action cycles of an endoscope system. In the fourth embodiment, the same components as those in the first to third embodiments will be denoted by the same reference numerals as the corresponding components in the first to third embodiments, and description thereof will be omitted and only differences from the first to third embodiments will be described mainly.

The endoscope system according to the present embodiment has the same configuration as the second embodiment, but differs in the control method. That is, according to the present embodiment, part of the procedures according to the third embodiment is automated and controlled by the shape-holding/air supply control apparatus 31 serving as control means. Thus, a control program which implements the control method described here differs from the one according to the second embodiment.

The control method will be described with reference to FIG. 24. In the present embodiment, since the control method differs from the one according to the second embodiment, functions assigned to the first to fourth switches 35a to 35d, respectively, also differ from those of the second embodiment.

Before the start of the action, the shape-holding section 1b of the endoscope 1 and shape-holding section 2b of the overtube 2 are both relaxed (made flexible) and the balloons 1a and 1b are both deflated, as in the case of the second embodiment.

When endoscopic procedures using the endoscope system are started, the surgeon inserts the overtube 2 by an appropriate length into the body cavity of the subject.

The surgeon presses the first switch 35a. Consequently, under the control of the main controller 32 which detects the press of the first switch 35a, the endoscope system performs a sequence of actions represented by the first iteration of symbols 35a1' and 35a2' in the first cycle in FIG. 24. That is, air is supplied from the air supply controller 34 to the balloon 2a of the overtube 2, inflating the balloon 2a as shown in FIG. 4 (symbol 35a1' in FIG. 24). Next, a drive signal is transmitted from the shape controller 33 to the shape-holding/relaxing drive section 27, causing the shape-holding section 1b of the endoscope 1 to relax (symbol 35a2' in FIG. 24). However, since the shape-holding section 1b remains relaxed immediately after the start of endoscopic procedures, practically nothing is done here. Incidentally, the inflation of the balloon 2a and the shape-holding of the shape-holding section 1b may be reversed in order.

Next, the surgeon presses the fourth switch 35d. Consequently, under the control of the main controller 32 which detects the press of the fourth switch 35d, the endoscope system performs a sequence of actions represented by the first iteration of symbols 35d1' and 35d2' in the first cycle in FIG. 24. That is, a drive signal is transmitted from the shape controller 33 to the shape-holding/relaxing drive section 27, causing the shape-holding section 2b to shape-hold as shown in FIG. 5 (symbol 35d1' in FIG. 24). Furthermore, although the endoscope system is designed to automatically perform the process of deflating the balloon 1a of the endoscope 1 under the control of the air supply controller 34 (symbol 35d2' in FIG. 24), since the balloon 1a remains deflated immediately after the start of endoscopic procedures, practically nothing is done here.

When the state shown in FIG. 5 is reached, the surgeon inserts the endoscope 1 into the overtube 2 to achieve the state shown in FIG. 6.

Next, the surgeon presses the third switch 35c. Consequently, under the control of the main controller 32 which detects the press of the third switch 35c, the endoscope system performs a sequence of actions represented by the first iteration of symbol 35c in the first cycle in FIG. 24. That is, air is supplied from the air supply controller 34 to the balloon 1a of the endoscope 1, inflating the balloon 1a as shown in FIG. 7. Next, a drive signal is transmitted from the shape controller 33 to the shape-holding/relaxing drive section 24, causing the shape-holding section 1b to shape-hold as shown in FIG. 8. Incidentally, the inflation of the balloon 1a and shape-holding of the shape-holding section 1b may be reversed in order.

When the state shown in FIG. 8 is reached, the surgeon may pull the endoscope 1 and thereby check whether the balloon 1a is fixed to the body cavity wall 19. However, this step may be omitted like the above case.

Subsequently, the surgeon presses the second switch 35b. Consequently, under the control of the main controller 32 which detects the press of the second switch 35b, the endoscope system performs a sequence of actions represented by symbol 35b in the first cycle in FIG. 24. That is, a drive signal is transmitted from the shape controller 33 to the shape-holding/relaxing drive section 27, causing the shape-holding section 2b of the overtube 2 to relax as shown in FIG. 9. Also, the air supply controller 34 sucks air from the balloon 2a of the overtube 2, deflating the balloon 2a as shown in FIG. 10.

Incidentally, the relaxation of the shape-holding section 2b and the deflation of the balloon 2a may be reversed in order.

When the state shown in FIG. 10 is reached, the surgeon inserts the overtube 2 over the endoscope 1 to achieve the state shown in FIG. 11.

Next, the surgeon presses the first switch 35a. Consequently, under the control of the main controller 32 which detects the press of the first switch 35a, the endoscope system performs a sequence of actions represented by the second iteration of symbols 35a1' and 35a2' in the first cycle in FIG. 24. That is, air is supplied from the air supply controller 34 to the balloon 2a of the overtube 2, inflating the balloon 2a as shown in FIG. 21 (symbol 35a1' in FIG. 24). Next, a drive signal is transmitted from the shape controller 33 to the shape-holding/relaxing drive section 27, causing the shape-holding section 1b of the endoscope 1 to relax as shown in FIG. 22 (symbol 35a2' in FIG. 24).

When the state shown in FIG. 22 is reached, the surgeon pulls the endoscope 1 and overtube 2 to haul in the body cavity wall 19 as shown in FIG. 23.

Next, when the surgeon presses the fourth switch 35d, the endoscope system performs a sequence of actions represented by the second iteration of symbols 35d1' and 35d2' in the first cycle in FIG. 24. Consequently, the balloon 1a of the endoscope 1 is deflated (FIG. 15) and the shape-holding section 2b of the overtube 2 shape-holds (FIG. 5).

Subsequently, a process in the second cycle is performed through repetition of the actions in FIG. 5→FIG. 6→FIG. 7→FIG. 8→FIG. 9→FIG. 10→FIG. 11→FIG. 21→FIG. 22→FIG. 23→FIG. 15→FIG. 5. Then, the same process as in the second cycle is repeated in the third and subsequent cycles.

Incidentally, the next operation to take may be indicated by display or by voice, as in the case of the second embodiment.

In this way, the fourth embodiment makes it possible to automatically control shape-holding and air supply according to predetermined procedures by simply pressing, for example, four switches in sequence, much in the same way as the second embodiment. In addition, according to the present embodiment, much in the same way as the third embodiment, when pulling the endoscope 1 and overtube 2 integrally, since the balloon 1a of the endoscope 1 and balloon 2a of the overtube 2 are in close contact with the body cavity wall 19, the surgeon can haul the body cavity wall 19 toward the hand side by holding the body cavity wall 19 more reliably.

[Fifth Embodiment]

Figure 25:
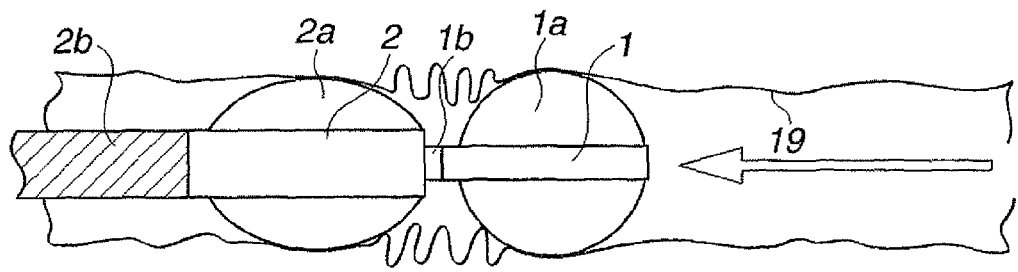
FIG. 25 is a diagram showing a sixth inserted state of an endoscope system according to a fifth embodiment of the present invention.
Figure 26:
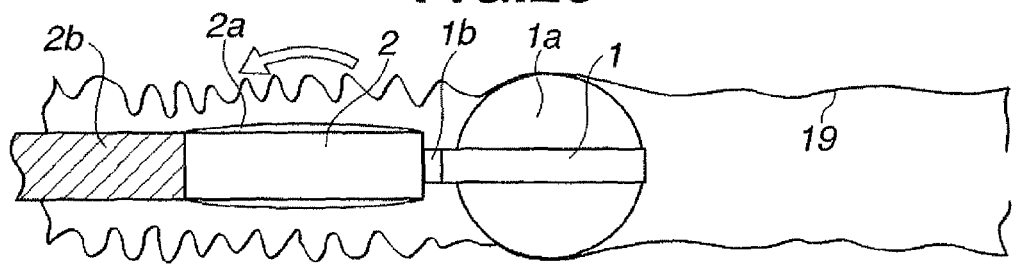
FIG. 26 is a diagram showing a seventh inserted state of the endoscope system according to the fifth embodiment.
Figure 27:
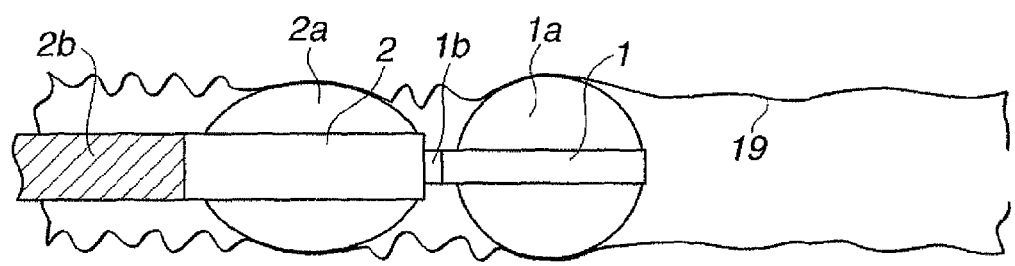
FIG. 27 is a diagram showing an eighth inserted state of the endoscope system according to the fifth embodiment.
Figure 28:
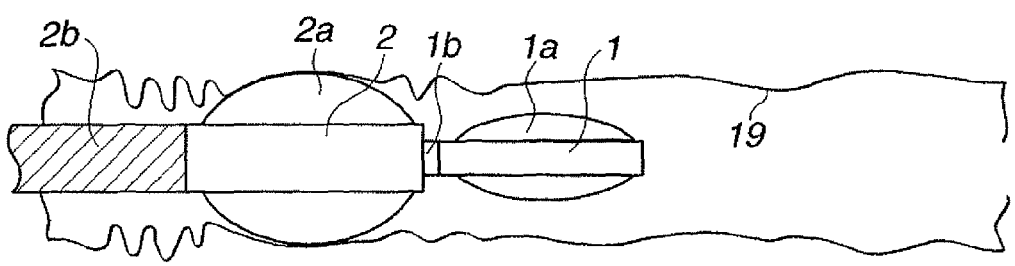
FIG. 28 is a diagram showing a ninth inserted state of the endoscope system according to the fifth embodiment.

FIGS. 25 to 28 show a fifth embodiment of the present invention, where FIG. 25 is a diagram showing a sixth inserted state of an endoscope system, FIG. 26 is a diagram showing a seventh inserted state of the endoscope system, FIG. 27 is a diagram showing an eighth inserted state of the endoscope system, and FIG. 28 is a diagram showing a ninth inserted state of the endoscope system.

In the fifth embodiment, the same components as those in the first to fourth embodiments will be denoted by the same reference numerals as the corresponding components in the first to fourth embodiments, and description thereof will be omitted and only differences from the first to fourth embodiments will be described mainly.

The endoscope system according to the present embodiment has the same configuration as the first embodiment, but differs in the method for use and in operating procedures from the first and third embodiments.

Once the surgeon starts insertion of the endoscope system, insertion procedures such as described with reference to FIG. 3 (first inserted state) to FIG. 7 (fifth inserted state) are carried out. It is assumed that the fifth inserted state shown in FIG. 7 has been reached.

Then, in the sixth inserted state shown in FIG. 25, the surgeon pulls only the endoscope 1 along the shape-held overtube 2. Consequently, the balloon 1a of the endoscope 1 approaches the balloon 2a of the overtube 2 in relative terms and that part of the body cavity wall 19 which is lying between the two balloons 1a and 2a is hauled in and shortened.

Next, in the seventh inserted state shown in FIG. 26, the balloon 2a of the overtube 2 is deflated. Consequently, the shortened part of the body cavity wall 19 between the two balloons 1a and 2a moves toward the hand side by getting over the outer periphery of the balloon 2a of the overtube 2.

Next, in the eighth inserted state shown in FIG. 27, the balloon 2a is inflated and brought into close contact with the body cavity wall 19 by being supplied with air.

Next, in the ninth inserted state shown in FIG. 28, the balloon 1a is deflated.

Subsequently, returning to the fourth inserted state shown in FIG. 6, the surgeon inserts the endoscope 1 into the overtube 2.

In this way, by repeating the procedures of FIG. 6→FIG. 7→FIG. 25→FIG. 26→FIG. 27→FIG. 28→FIG. 6, it is possible to gradually haul the body cavity wall 19 to the hand side of the balloon 2a of the overtube 2. Consequently, the endoscope 1 advances relative to the body cavity wall 19.

The fifth embodiment offers substantially the same effect as the first to fourth embodiments also by hauling in the body cavity wall 19 by pulling only the endoscope 1 with the balloon 1a inflated. The repeated procedures of FIG. 6→FIG. 7→FIG. 25→FIG. 26→FIG. 27→FIG. 28→FIG. 6 eliminate the needs to shape-hold the endoscope 1 and relax the overtube 2 and basically eliminate the need for the surgeon to insert the overtube 2, making it possible to simplify operation. Furthermore, when the endoscope 1 is pulled, the overtube 2, which is shape-held, serves as a guide, making it easy to perform the pull action.

Again in the present embodiment, although not illustrated, part of the endoscopic procedures can be automated using the configuration described in the second embodiment, as in the case of the second embodiment in relation to the first embodiment or the fourth embodiment in relation to the third embodiment.

[Sixth Embodiment]

Figure 29:
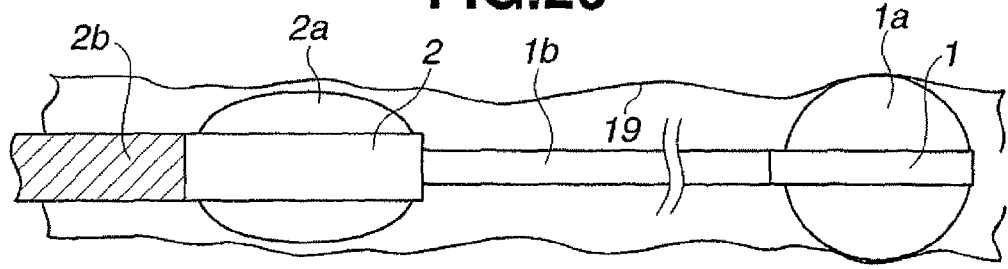
FIG. 29 is a diagram showing a sixth inserted state of an endoscope system according to a sixth embodiment of the present invention.
Figure 30:
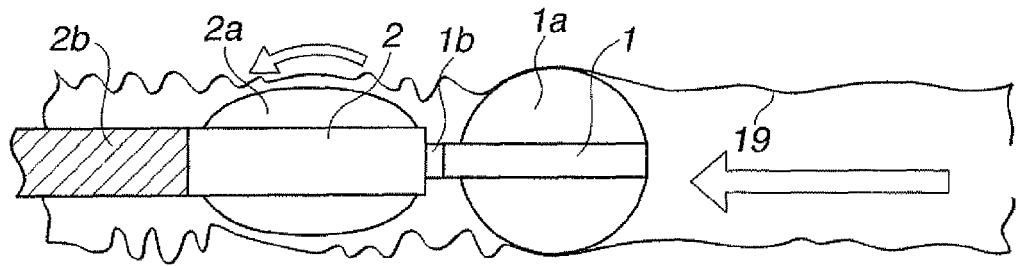
FIG. 30 is a diagram showing a seventh inserted state of the endoscope system according to the sixth embodiment.

FIGS. 29 and 30 show a sixth embodiment of the present invention, where FIG. 29 is a diagram showing a sixth inserted state of an endoscope system and FIG. 30 is a diagram showing a seventh inserted state of the endoscope system. In the sixth embodiment, the same components as those in the first to fifth embodiments will be denoted by the same reference numerals as the corresponding components in the first to fifth embodiments, and description thereof will be omitted and only differences from the first to fifth embodiments will be described mainly.

The endoscope system according to the present embodiment has the same configuration as the first embodiment, but slightly differs in the method for use from the fifth embodiment.

Once the surgeon starts insertion of the endoscope system, insertion procedures such as described with reference to FIG. 3 (first inserted state) to FIG. 7 (fifth inserted state) are carried out. It is assumed that the fifth inserted state shown in FIG. 7 has been reached.

In the sixth inserted state in FIG. 29, the balloon 2a serving as fixing means of the overtube 2 is deflated by a predetermined amount (slightly) (to bring the balloon 2a closer to a non-fixing state than to a fixing state by a predetermined amount). After the slight deflation, preferably the balloon 2a remains inflated to such an extent as to hold that part of the body cavity wall 19 which is lying on the hand side of the balloon 2a while allowing the body cavity wall 19 which is subsequently hauled in by the balloon 1a of the endoscope 1 to get over the balloon 2a.

Next, in the seventh inserted state in FIG. 30, the surgeon pulls only the endoscope 1 along the shape-held overtube 2. Consequently, the balloon 1a of the endoscope 1 approaches the balloon 2a of the overtube 2 in relative terms and the body cavity wall 19 is hauled toward the hand side. At this time, since the balloon 2a of the overtube 2 remains inflated to the extent described above, the body cavity wall 19 hauled in by the balloon 1a is further hauled toward the hand side by getting over the outer periphery of the balloon 2a. Consequently, that part of the body cavity wall 19 which is lying between the two balloons 1a and 2a is shortened to a lesser extent than in the example according to the fifth embodiment in FIG. 25.

Next, in the eighth inserted state in FIG. 27, the balloon 2a is inflated to a diameter approximately equal to that of the balloon 1a and brought into close contact with the body cavity wall 19 securely by being supplied with air.

Next, in the ninth inserted state in FIG. 28, the balloon 1a is deflated.

Subsequently, returning to the fourth inserted state in FIG. 6, the surgeon inserts the endoscope 1 into the overtube 2.

In this way, by repeating the procedures of FIG. 6→FIG. 7→FIG. 29→FIG. 30→FIG. 27→FIG. 28→FIG. 6, it is possible to gradually haul the body cavity wall 19 to the hand side of the balloon 2a of the overtube 2. Consequently, the endoscope 1 advances relative to the body cavity wall 19.

The sixth embodiment offers substantially the same effect as the fifth embodiment. In addition, since the balloon 2a of the overtube 2 is inflated to a slightly lesser extent, the body cavity wall 19 being hauled in by the balloon 1a of the endoscope 1 can get over the balloon 2a, allowing the body cavity wall 19 to be shortened to a lesser extent. This makes it possible to reduce the burden on the subject.

Again in the present embodiment, although not illustrated, part of the endoscopic procedures can be automated using the configuration described in the second embodiment, as in the case of the second embodiment in relation to the first embodiment or the fourth embodiment in relation to the third embodiment.

[Seventh Embodiment]

Figure 31:
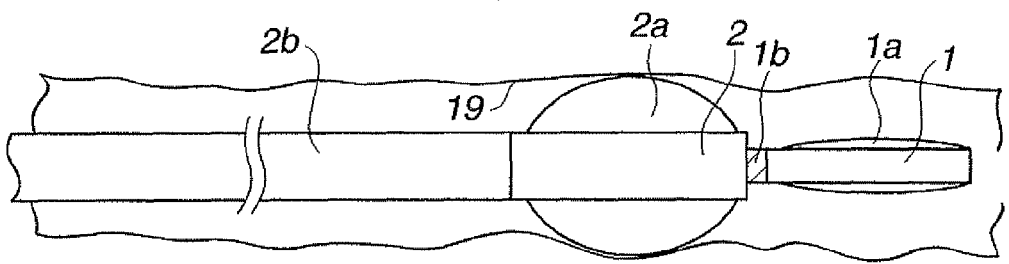
FIG. 31 is a diagram showing an eleventh inserted state of an endoscope system according to a seventh embodiment.
Figure 32:
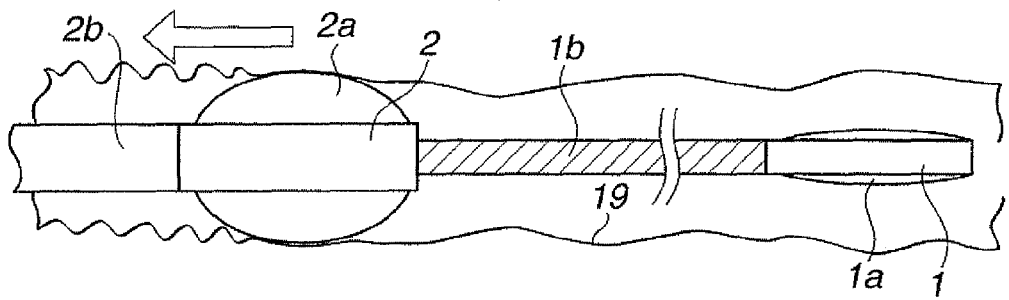
FIG. 32 is a diagram showing a twelfth inserted state of the endoscope system according to the seventh embodiment.

FIGS. 31 and 32 show a seventh embodiment of the present invention, where FIG. 31 is a diagram showing an eleventh inserted state of an endoscope system and FIG. 32 is a diagram showing a twelfth inserted state of the endoscope system. In the seventh embodiment, the same components as those in the first to sixth embodiments will be denoted by the same reference numerals as the corresponding components in the first to sixth embodiments, and description thereof will be omitted and only differences from the first to sixth embodiments will be described mainly.

The endoscope system according to the present embodiment has the same configuration as the first embodiment, but differs in the method for use and in operating procedures from the first, third, fifth, and sixth embodiments.

Once the surgeon starts insertion of the endoscope system, insertion procedures such as described with reference to FIG. 3 (first inserted state) to FIG. 11 (ninth inserted state) and FIG. 21 (tenth inserted state) are carried out. It is assumed that the tenth inserted state shown in FIG. 21 has been reached.

In the eleventh inserted state in FIG. 31, the balloon 1a of the endoscope 1 is deflated.

Next, in the twelfth inserted state in FIG. 32, the surgeon pulls only the overtube 2 along the shape-held endoscope 1. Consequently, the balloon 2a of the overtube 2 moves toward the hand side, hauling the body cavity wall 19 toward the hand side.

Subsequently, returning to the seventh inserted state shown in FIG. 9, the balloon 1a of the endoscope 1 is inflated.

In this way, by repeating the procedures of FIG. 9→FIG. 10→FIG. 11→FIG. 21→FIG. 31→FIG. 32→FIG. 9, it is possible to gradually haul the body cavity wall 19 to the hand side of the balloon 2a of the overtube 2. Consequently, the endoscope 1 advances relative to the body cavity wall 19.

The seventh embodiment offers substantially the same effect as the first to sixth embodiments also by hauling in the body cavity wall 19 by pulling only the overtube 2 with the balloon 2a inflated. The repeated procedures of FIG. 9→FIG. 10→FIG. 11→FIG. 21→FIG. 31→FIG. 32→FIG. 9 eliminate the needs to shape-hold the overtube 2 and relax the endoscope 1 and basically eliminate the need for the surgeon to insert the endoscope 1, making it possible to simplify operation. Furthermore, when the overtube 2 is pulled, the endoscope 1, which is shape-held, serves as a guide, making it easy to perform the pull action.

Again in the present embodiment, although not illustrated, part of the endoscopic procedures can be automated using the configuration described in the second embodiment, as in the case of the second embodiment in relation to the first embodiment or the fourth embodiment in relation to the third embodiment.

Next, a configuration example of the endoscope system will be described with reference to FIGS. 33 to 37.

Figure 33:
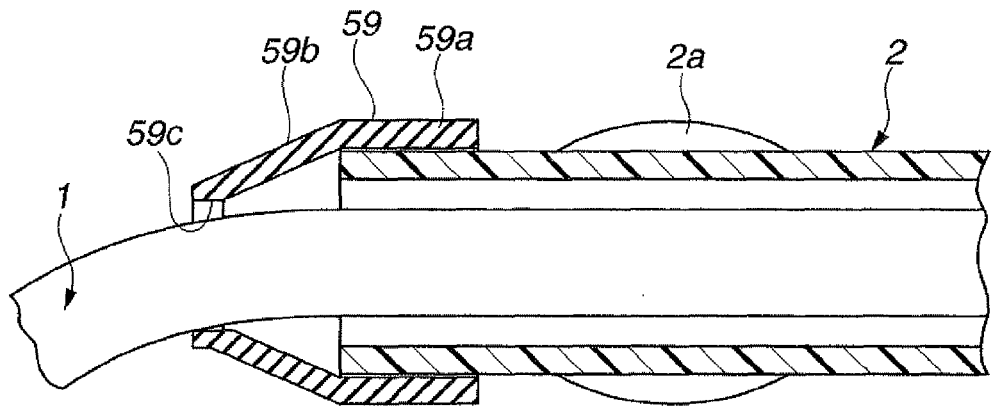
FIG. 33 is a diagram showing an example of a conventional hood mounted at the distal end of an overtube.
Figure 34:
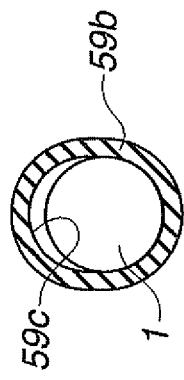
FIG. 34 is a diagram showing how a gap is created between a conventional hood and endoscope by bending of the endoscope.

FIG. 33 is a diagram showing an example of a conventional hood mounted at the distal end of an overtube and FIG. 34 is a diagram showing how a gap is created between the conventional hood and endoscope by bending of the endoscope.

To improve the capability of the endoscope 1 to advance and retract in the overtube 2, the overtube 2 is configured to have an inside diameter larger than an outside diameter of the endoscope 1 by a predetermined amount, thereby providing a gap between the inside diameter of the overtube 2 and outside diameter of the endoscope 1. On the other hand, it is likely that this configuration will cause the body cavity wall 19 to get into the gap between the endoscope 1 and overtube 2 when the endoscope 1 is pulled back into the overtube 2. Thus, a hood 59 is attached to the distal end of the overtube 2 to substantially eliminate a gap between the tip of the hood 59 and outside diameter of the endoscope 1.

That is, the conventional hood 59 which is approximately cylindrical in shape includes a cylindrical mount 59a to be fitted over the tip of the overtube 2 and a taper 59b which decreases in diameter from the mount 59a to the distal end, in which an inside diameter of an opening 59c at the distal end of the taper 59b is approximately equal to an outside diameter of the endoscope 1. The conventional hood 59 is made of a soft material such as silicon rubber.

However, the use of the hood 59 made of such a soft material may cause a gap to be created between the opening 59c at the distal end of the hood 59 and endoscope 1 when bending is applied to the endoscope 1 as shown in FIGS. 33 and 34.

Figure 35:
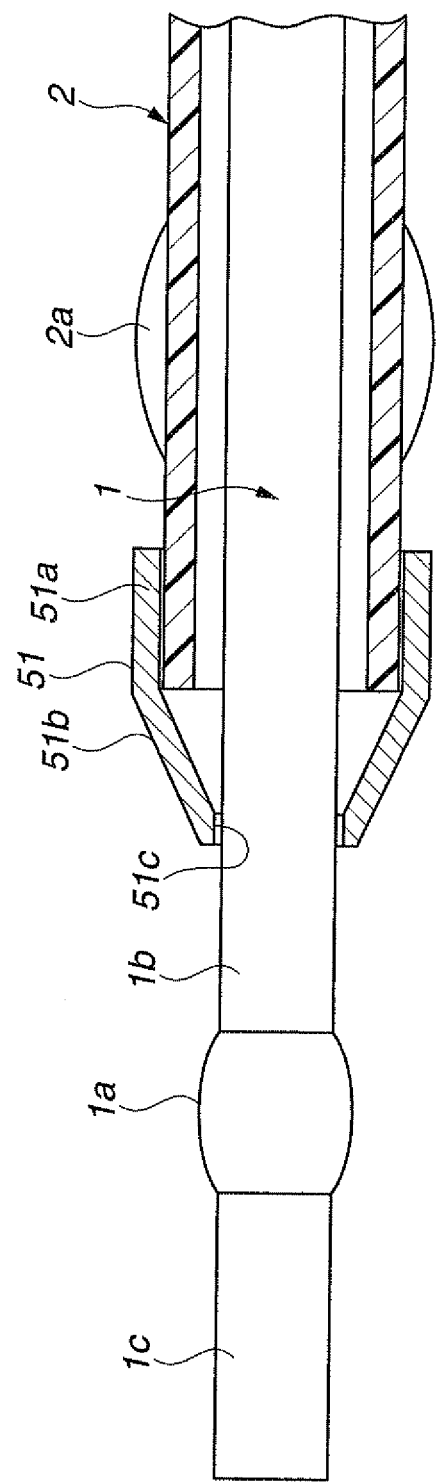
FIG. 35 is a diagram showing an example of a hood improved to be applicable to various embodiments.

A hood 51 improved to fix the above problem is shown in FIG. 35. That is, FIG. 35 is a diagram showing an example of a hood improved to be applied to various embodiments.

The hood 51 has substantially the same structure as the conventional hood 59 described above. That is, the hood 51 which is approximately cylindrical in shape includes a cylindrical mount 51a to be fitted over the tip of the overtube 2 and a taper 51b which decreases in diameter from the mount 51a to the distal end, in which an inside diameter of an opening 51c at the distal end of the taper 51b is approximately equal to (to be exact, slightly larger than) the outside diameter of the endoscope 1. However, unlike the conventional hood 59, the hood 51 is made of a hard material such as hard rubber, resin, or metal. Also, an inner surface of the opening 51c at the distal end has been treated to reduce frictional resistance with an outer surface of the endoscope 1.

With the above configuration, the hood 51 itself does not deform even if bending is applied to the endoscope 1, but also prevents that part of the endoscope 1 which is located in the hood 51 and overtube 2 from bending, and thus there is no possibility that a gap such as shown in FIGS. 33 and 34 will be created. This makes it possible to prevent the body cavity wall 19 from getting into the gap between the endoscope 1 and overtube 2 when the endoscope 1 is advanced and retracted relative to the overtube 2, and simplify operation by eliminating concerns during the operation.

Figure 36:
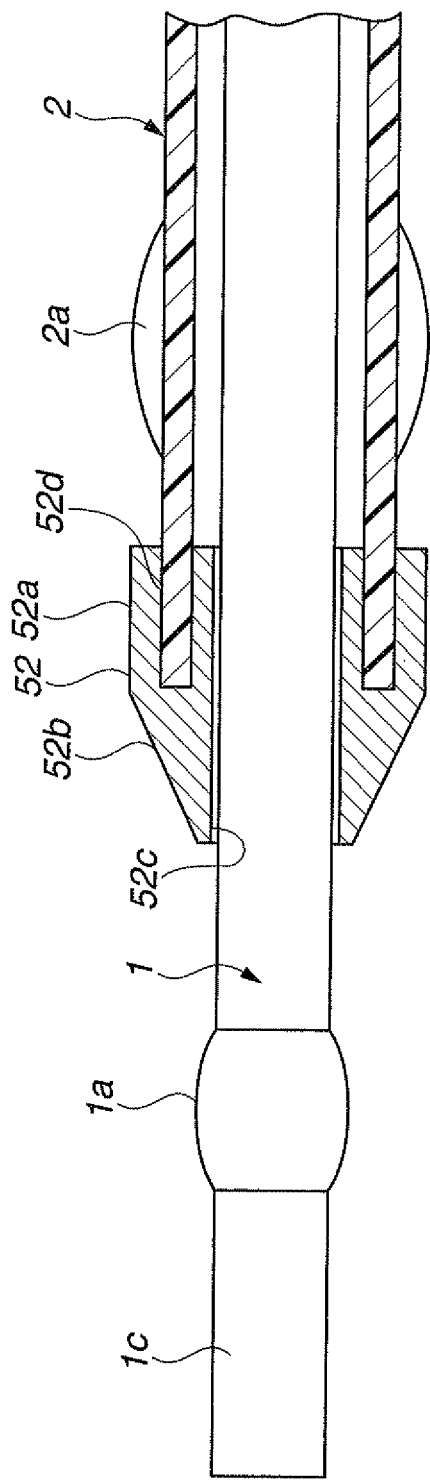
FIG. 36 is a diagram showing another example of a hood improved to be applicable to various embodiments.

FIG. 36 is a diagram showing another example of a hood improved to be applied to various embodiments.

A hood 52 here is equipped with a shape restricting section which restricts bending of the endoscope 1. That is, the hood 52 is made of a hard material such as hard rubber, resin, or metal and includes a cylindrical mount 52a and a taper 52b which decreases in diameter from the mount 52a to the distal end. A circular hole 52c serving as the shape restricting section is formed in common to the mount 52a and taper 52b. An inside diameter of the circular hole 52c is approximately equal to (to be exact, slightly larger than) the outside diameter of the endoscope 1. Also, an inner surface of the circular hole 52c has been treated to reduce frictional resistance with the outer surface of the endoscope 1. Furthermore, a circular groove 52d concentric with the circular hole 52c is formed in an outer periphery of the circular hole 52c, extending forward from a rear end face of the mount 52a, to accept the distal end of the overtube 2.

The hood 52 configured as described above prevents bending from being applied to the endoscope 1 because the circular hole 52c has a predetermined length in the axial direction. Since the bending itself of the endoscope 1 is restricted, it is possible to prevent a gap such as shown in FIGS. 33 and 34 from being created between the circular hole 52c of the hood 52 and the endoscope 1.

The configuration shown in FIG. 36 not only offers substantially the same effect as the configuration shown in FIG. 35, but also restricts bending of the endoscope 1 and thereby prevents gap formation more reliably.

Figure 37:
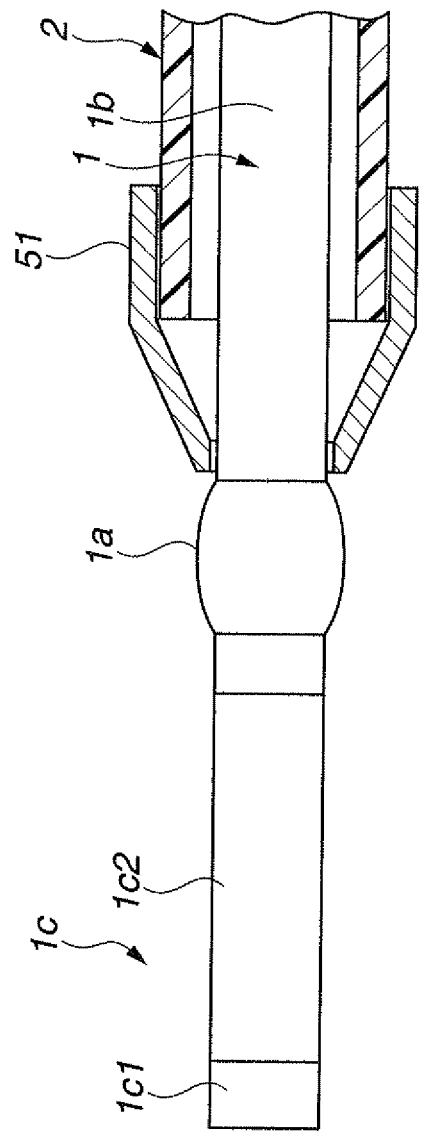
FIG. 37 is a diagram showing, in more detail, a configuration of a bending portion/distal end portion provided beyond a balloon and applicable to various embodiments. C-b1

As described earlier, according to the first embodiment, the bending portion/distal end portion 1c is provided beyond the balloon 1a in the insertion section of the endoscope 1. FIG. 37 is a diagram showing a configuration of the bending portion/distal end portion 1c provided beyond the balloon 1a in more detail.

As shown in FIG. 37, the bending portion/distal end portion 1c provided beyond the balloon 1a includes a distal end portion (distal rigid portion) 1c1 and bending portion 1c2 provided in a row from the distal end to the near end.

In this configuration, it is recommended to keep the balloon inflated to the extent shown in FIG. 37 even when the balloon 1a is not used to hold the body cavity wall 19. Consequently, even if there is an attempt to pull the endoscope 1 into the overtube 2, the balloon 1a will hit the hood S1 attached to the distal end of the overtube 2, restricting a further pull. Thus, the bending portion 1c2 will never get into the hood 51 or overtube 2, causing no bending at the location of the hood 51. This reliably prevents formation of a gap such as described with reference to FIGS. 33 and 34.

In the embodiments described above, the balloons 1a and 2a are approximately equal in diameter when inflated except for the parts shown in FIGS. 29 and 30 in the sixth embodiment. However, the first embodiment, seventh embodiment and the like, for example, are not limited to this. For example, the balloon 2a may be larger in diameter than the balloon 1a when inflated. That is, for example, the force required by the balloon 2a to hold the body cavity wall 19 in the state in FIG. 32 according to the seventh embodiment is believed to be larger than the force required by the balloon 1a to hold the body cavity wall 19 in the state in FIG. 10 cited in the seventh embodiment. This is because the body cavity wall 19 contracted to the position of the balloon 2a in the state shown in FIG. 32 returns to the position of the balloon 1a in the state shown in FIG. 10, meaning that the body cavity wall 19 is contracted to a greater extent in FIG. 32 than in FIG. 10. Thus, in order to exert a greater holding force, it is effective to make the diameter of the inflated balloon 2a larger than the diameter of the inflated balloon 1a.

Furthermore, the extent to which the balloon 1a and 2a (either both or one of them) are inflated may be varied based on information—such as described below—possessed by the shape-holding/air supply control apparatus 31.

A first example involves increasing the extent to which the balloon used to haul in the body cavity wall 19 is inflated with increases in the number of times the balloon is inflated.

A second example involves increasing the extent to which the balloon is inflated with increases in the number of times (cycles) a series of procedures is repeated to haul in the body cavity wall 19.

A third example involves increasing the extent to which the balloon is inflated with increases in time after the start of endoscopic procedures. The time after the start of endoscopic procedures may be measured, for example, as time after startup of the shape-holding/air supply control apparatus 31.

Possible methods for controlling the extent to which the balloon is inflated include a method which uses supply air volume, air supply time, and air supply pressure as control parameters.

In this way, by increasing the diameter of the inflated balloon with increases in the amount of body cavity wall 19 to be hauled in, it is possible to hold the body cavity wall 19 more reliably.

Although the endoscope system configured as described above allows a single surgeon to perform the operation of advancing and retracting the endoscope 1, operation of shape-holding and relaxing the endoscope 1, operation of advancing and retracting the overtube 2, operation of shape-holding and relaxing the overtube 2, and operation of carrying out observation and treatment by the endoscope 1, any one or more of these operations may be performed with the help of one or more assistants. Thus, any of the operations may be performed by one or more persons.

The present invention is not limited to the above embodiments, and needless to say, various modifications and applications are possible without departing from the spirit of the present invention.

[Annex]

The embodiments of the present invention described above provide the following methods.

1A. A method for using an endoscope system which includes a first elongate member inserted into a subject, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, and second fixing means which, being provided at the distal end of the second elongate member, fixes the second elongate member to the subject by abutting the subject, the method comprising the steps of:

advancing the second elongate member in the direction of the passage with the second fixing means being in a non-fixing state;

advancing the first elongate member in the direction of the passage with the first fixing means being in a non-fixing state;

putting at least one of the first fixing means and the second fixing means in a fixing state; and pulling the first elongate member and the second elongate member integrally when at least one of the first fixing means and the second fixing means is in a fixing state.

2A. The method for using an endoscope system according to annex 1A, wherein:

the step of putting at least one of the first fixing means and the second fixing means in a fixing state is a step of putting both the first fixing means and the second fixing means in a fixing state; and the step of pulling the first elongate member and the second elongate member integrally when at least one of the first fixing means and the second fixing means is in a fixing state is a step of pulling the first elongate member and the second elongate member integrally when both the first fixing means and the second fixing means are in a fixing state, 3A. A method for using an endoscope system which includes a first elongate member inserted into a subject, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, and second fixing means which, being provided at the distal end of the second elongate member, fixes the second elongate member to the subject by abutting the subject, the method comprising the steps of:

advancing the second elongate member in the direction of the passage with the second fixing means being in a non-fixing state when the first fixing means is in a fixing state;

putting the second fixing means in a fixing state;

putting the first fixing means in a non-fixing state;

advancing the first elongate member in the direction of the passage with the first fixing means being in the non-fixing state;

pulling the first elongate member and the second elongate member integrally when the second fixing means is in the fixing state;

pulling the first fixing means in a fixing state; and putting the second fixing means in a non-fixing state.

4A. A method for using an endoscope system which includes a first elongate member inserted into a subject, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, and second fixing means which, being provided at the distal end of the second elongate member, fixes the second elongate member to the subject by abutting the subject, the method comprising the steps of:

advancing the second elongate member in the direction of the passage with the second fixing means being in a non-fixing state when the first fixing means is in a fixing state;

putting the second fixing means in a fixing state;

putting the first fixing means in a non-fixing state;

advancing the first elongate member in the direction of the passage with the first fixing means being in the non-fixing state;

putting the first fixing means in a fixing state;

pulling the first elongate member and the second elongate member integrally when the first fixing means and the second fixing means are in the fixing state; and putting the second fixing means in a non-fixing state.

5A. The method for using an endoscope system according to annex 1A, 3A, or 4A, wherein the endoscope system further includes a first shape-holding section provided on the first elongate member and capable of switching at least part of the first elongate member between a flexible and deformable first state and a shape-held second state, and a second shape-holding section provided on at least part of the second elongate member in such a way as to include at least part of a portion which can stick out of the distal opening and capable of switching the at least part of the second elongate member between a flexible and deformable first state and a shape-held second state, the method further comprising the steps of:

putting the first shape-holding section in the second state and putting the second shape-holding section in the first state before the step of advancing the second elongate member in the direction of the passage;

putting the second shape-holding section in the second state and putting the first shape-holding section in the first state before the step of advancing the first elongate member in the direction of the passage; and putting the first shape-holding section and the second shape-holding section in the first state before the step of pulling the first elongate member and the second elongate member integrally.

6A. A method for using an endoscope system which includes a first elongate member inserted into a subject, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, and second fixing means which, being provided at the distal end of the second elongate member, fixes the second elongate member to the subject by abutting the subject, the method comprising the steps of:

advancing the second elongate member in the direction of the passage with the second fixing means being in a non-fixing state when the first fixing means is in a fixing state;

putting the second fixing means in a fixing state;

pulling only the second elongate member when the second fixing means is in the fixing state;

putting the first fixing means in a non-fixing state;
putting the first fixing means in a fixing state; and
putting the second fixing means in a non-fixing state.

7A. A method for using an endoscope system which includes a first elongate member inserted into a subject, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, and second fixing means which, being provided at the distal end of the second elongate member, fixes the second elongate member to the subject by abutting the subject, the method comprising the steps of:

advancing the second elongate member in the direction of the passage with the second fixing means being in a non-fixing state when the first fixing means is in a fixing state;

putting the second fixing means in a fixing state;

bringing the first fixing means closer to a non-fixing state than to the fixing state by a predetermined amount;

pulling only the second elongate member when the second fixing means is in the fixing state;

putting the first fixing means in a fixing state; and
putting the second fixing means in a non-fixing state.

8A. The method for using an endoscope system according to annex 6A or 7A, wherein:

the endoscope system further includes a first shape-holding section provided on the first elongate member and capable of switching at least part of the first elongate member between a flexible and deformable first state and a shape-held second state, and a second shape-holding section provided on at least part of the second elongate member in such a way as to include at least part of a portion which can stick out of the distal opening and capable of switching the at least part of the second elongate member between a flexible and deformable first state and a shape-held second state; and the step of advancing the second elongate member in the direction of the passage and the step of pulling only the second elongate member are carried out when the second shape-holding section is in the first state and the first shape-holding section is in the second state.

9A. A method for using an endoscope system which includes a first elongate member inserted into a subject, first fixing means which, being provided at a distal end of the first elongate member, fixes the first elongate member to the subject by abutting the subject, a conduit which, being provided on the first elongate member, communicates a proximal opening and a distal opening of the first elongate member, a second elongate member which is inserted through the proximal opening, passed through the conduit in such a way that a distal end of the second elongate member can stick out of the distal opening, and movable relative to the first elongate member in a direction of the passage, and second fixing means which, being provided at the distal end of the second elongate member, fixes the second elongate member to the subject by abutting the subject, the method comprising the steps of:

advancing the first elongate member in the direction of the passage with the first fixing means being in a non-fixing state when the second fixing means is in a fixing state;

putting the first fixing means in a fixing state;
putting the second fixing means in a non-fixing state;

pulling only the first elongate member when the second fixing means is in the non-fixing state and the first fixing means in the fixing state;

putting the second fixing means in a fixing state; and
putting the first fixing means in a non-fixing state 10A. The method for using an endoscope system according to annex 9A, wherein the endoscope system further includes a first shape-holding section provided on the first elongate member and capable of switching at least part of the first elongate member between a flexible and deformable first state and a shape-held second state, and a second shape-holding section provided on at least part of the second elongate member in such a way as to include at least part of a portion which can stick out of the distal opening and capable of switching the at least part of the second elongate member between a flexible and deformable first state and a shape-held second state; and the step of advancing the first elongate member in the direction of the passage and the step of pulling only the first elongate member are carried out when the first shape-holding section is in the first state and the second shape-holding section is in the second state.

1B. A method for using an endoscope system which includes an endoscope equipped with a balloon and an overtube equipped with a balloon, the method comprising the steps of:

advancing the endoscope whose balloon is deflated;
advancing the overtube whose balloon is deflated;
inflating the balloon of at least one of the endoscope and overtube; and pulling the endoscope and the overtube integrally with at least one of the balloons inflated.

2B. The method for using an endoscope system according to annex 1B, wherein:

the step of inflating the balloon of at least one of the endoscope and overtube is a step of inflating the balloons of both the endoscope and overtube; and the step of pulling the endoscope and the overtube integrally with at least one of the balloons inflated is a step of pulling the endoscope and the overtube integrally with both the balloons inflated.

3B. A method for using an endoscope system which includes an endoscope equipped with a balloon and an overtube equipped with a balloon, the method comprising the steps of:

advancing the endoscope whose balloon is deflated with the balloon of the overtube inflated;

inflating the balloon of the endoscope;
deflating the balloon of the overtube;
advancing the overtube whose balloon is deflated;
pulling the endoscope and the overtube integrally with the balloon of the endoscope inflated;
inflating the balloon of the overtube; and
deflating the balloon of the endoscope, 4B. A method for using an endoscope system which includes an endoscope equipped with a balloon and an overtube equipped with a balloon, the method comprising the steps of:

advancing the endoscope whose balloon is deflated with the balloon of the overtube inflated;

inflating the balloon of the endoscope;
deflating the balloon of the overtube;
advancing the overtube whose balloon is deflated;
inflating the balloon of the overtube;
pulling the endoscope and the overtube integrally with the balloons of both the overtube and the endoscope inflated; and
deflating the balloon of the endoscope.

5B. The method for using an endoscope system according to annex 1B, 3B, or 4B, wherein the endoscope and the overtube are configured to be able to shape-hold and relax, the method further comprising the steps of:

shape-holding the overtube and relaxing the endoscope before the step of advancing the endoscope;

shape-holding the endoscope and relaxing the overtube before the step of advancing the overtube; and relaxing the endoscope and the overtube before the step of pulling the endoscope and the overtube integrally.

6B. A method for using an endoscope system which includes an endoscope equipped with a balloon and an overtube equipped with a balloon, the method comprising the steps of:

advancing the endoscope whose balloon is deflated with the balloon of the overtube inflated;

inflating the balloon of the endoscope;

pulling only the endoscope with the balloon of the endoscope inflated;

deflating the balloon of the overtube;

inflating the balloon of the overtube; and deflating the balloon of the endoscope.

7B. A method for using an endoscope system which includes an endoscope equipped with a balloon and an overtube equipped with a balloon, the method comprising the steps of:

advancing the endoscope whose balloon is deflated with the balloon of the overtube inflated;

inflating the balloon of the endoscope;

deflating the balloon of the overtube by a predetermined amount from an inflated state;

pulling only the endoscope with the balloon of the endoscope inflated;

inflating the balloon of the overtube; and deflating the balloon of the endoscope 8B. The method for using an endoscope system according to annex 6B or 7B, wherein:

the endoscope and the overtube are configured to be able to shape-hold and relax; and the step of advancing the endoscope and the step of pulling only the endoscope are carried out with the endoscope relaxed and with the overtube shape-held.

9B. A method for using an endoscope system which includes an endoscope equipped with a balloon and an overtube equipped with a balloon, the method comprising the steps of:

advancing the overtube whose balloon is deflated with the balloon of the endoscope inflated;

inflating the balloon of the overtube;

deflating the balloon of the endoscope;

pulling only the overtube with the balloon of the endoscope deflated and with the balloon of the overtube inflated;

inflating the balloon of the endoscope; and deflating the balloon of the overtube.

10B. The method for using an endoscope system according to annex 9B, wherein:

the endoscope and the overtube are configured to be able to shape-hold and relax; and the step of advancing the overtube and the step of pulling only the overtube are carried out with the overtube relaxed and with the endoscope shape-held.

Note that the present application claims priority right pursuant to international application PCT/JP2005/008912 filed, May 16, 2005, under the Patent Cooperation Treaty. The contents of the application are incorporated in the specification, claims, and drawings herein by reference.

The invention claimed is:

1. An endoscope system comprising:

a first elongate member inserted into a subject;

a first shape-holding section provided on the first elongate member and capable of switching at least part of the first elongate member between a flexible and deformable first state and a shape-held second state;

first fixing means which, being provided at a distal end of the first elongate member, fixes the first elongate member to the subject by abutting the subject;

a conduit which, being provided on the first elongate member, communicates a proximal opening and a distal opening of the first elongate member;

a second elongate member which is inserted through the proximal opening, passed through the conduit in such a way that a distal end of the second elongate member can stick out of the distal opening, and movable relative to the first elongate member in a direction of the conduit;

a second shape-holding section provided on at least part of the second elongate member in such a way as to include at least part of a portion which can stick out of the distal opening and capable of switching the at least part of the second elongate member between a flexible and deformable first state and a shape-held second state; and second fixing means which, being provided at the distal end of the second elongate member, fixes the second elongate member to the subject by abutting the subject;

wherein the first fixing means is provided beyond the first shape-holding section of the first elongate member and is not provided at the first shape-holding section;

wherein the second fixing means is provided beyond the second shape-holding section of the second elongate member and is not provided at the second shape-holding section;

wherein the endoscope system further comprises a control means which switches the second shape-holding section between the first state and the second state and fixes and unfixes the second elongate member to the subject by the second fixing means;

wherein the control means switches the second shape-holding section from the second state to the first state with the second elongate member fixed to the subject by the second fixing means;

wherein the first fixing means and the second fixing means are both balloons; and wherein the first fixing means when inflated is in diameter larger than the second fixing means when inflated.

2. The endoscope system according to claim 1, wherein the first elongate member is an insertion section of an endoscope.

3. The endoscope system according to claim 1, wherein the second elongate member is an insertion section of an endoscope.

4. The endoscope system according to claim 1, further comprising guiding means which gives guidance as to a next operating step to be taken, wherein the control means further controls the guidance of the guiding means.

5. The endoscope system according to claim 4, wherein the guiding means is display means which gives guidance by means of display.

6. The endoscope system according to claim 4, wherein the guiding means is voice means which gives guidance by voice.

7. The endoscope system according to claim 1, wherein, after at least one of the first fixing means and the second fixing means initially abuts the subject, at least one of the first fixing means and the second fixing means continues to abut the subject.

8. The endoscope system according to claim 1, wherein, after at least one of the first fixing means and the second fixing means initially abuts the subject, only one of the first elongate member and the second elongate member advances in an insertion direction with respect to the subject at any given time.

9. The endoscope system according to claim 8, wherein, after at least one of the first fixing means and the second fixing means initially abuts the subject, the one of the first fixing means and the second fixing means which is associated with the one of the first elongate member and the second elongate member which does not advance with respect to the subject continuously abuts the subject.

10. The endoscope system according to claim 9, wherein, after at least one of the first fixing means and the second fixing means initially abuts the subject, the one of the first elongate member and the second elongate member which does not advance with respect to the subject is placed into the shape-held second state.

11. The endoscope system according to claim 1, wherein:
when the first fixing means abuts the subject and the first elongate member pulls the subject the first elongate member is in the flexible and deformable first state; and
when the second fixing means abuts the subject and the second elongate member pulls the subject the second elongate member is in the flexible and deformable first state.

12. The endoscope system according to claim 1, wherein the second fixing means has a shape for restricting the pulling of the second elongate member into the conduit when the second fixing means does not abut the subject.

13. The endoscope system according to claim 1, wherein a force of the first fixing means abutting the subject is larger than a force of the second fixing means abutting the subject.

14. The endoscope system according to claim 1, wherein at least one of:
(a) a force of the first fixing means abutting the subject increases as a number of cycles between the first fixing means abutting the subject and the first fixing means not abutting the subject increases; and
(b) a force of the second fixing means abutting the subject increases as a number of cycles between the second fixing means abutting the subject and the second fixing means not abutting the subject increases.

* * * * *